United States Patent
Billhardt-Troughton et al.

Patent Number: 5,424,311
Date of Patent: Jun. 13, 1995

[54] AZAQUINOXALINES AND THEIR USE

[75] Inventors: Uta-Maria Billhardt-Troughton, Raleigh, N.C.; Manfred Rösner, Eppstein/Taunus, Germany; Rudolf Bender, Bad Soden am Taunus, Germany; Christoph Meichsner, Liederbach, Germany

[73] Assignee: Hoechst Aktiengesellschaft, Frankfurt am Main, Germany

[21] Appl. No.: 125,163

[22] Filed: Sep. 23, 1993

[30] Foreign Application Priority Data

Sep. 26, 1992 [DE] Germany ............... 42 32 392.4

[51] Int. Cl.⁶ .............. C07P 241/00; A61K 31/495
[52] U.S. Cl. ..................... 514/248; 544/350
[58] Field of Search ............. 514/248; 544/350

[56] References Cited

U.S. PATENT DOCUMENTS 4,077,955  3/1978  Denzel et al. ............... 260/250 BC

FOREIGN PATENT DOCUMENTS

| | | |
|---|---|---|
| 0010426A1 | 4/1980 | European Pat. Off. |
| 0162776B1 | 11/1985 | European Pat. Off. |
| 0311378A3 | 4/1989 | European Pat. Off. |
| 0320136A3 | 6/1989 | European Pat. Off. |
| 0509398A1 | 10/1992 | European Pat. Off. |

OTHER PUBLICATIONS

Berner et al., Journal of Medicinal Chemistry (1973) 16(11) 1296–1298.

M. A. Verini et al., Antiviral Activity of a Pyrazino–Pyrazine Derivative, Chemotherapy 21: 221–230 (1975).

H. Berner et al., Antivirals 1, Journal of Medicinal Chemistry, (1973), vol. 16, No. 11, 1296–1298.

Taylor et al., "Pteridines. XXXVI. Syntheses of Xanthopterin and Isoxanthopterin. Application of N-Oxide Chemistry to Highly Functionalized Pyrazines and Pteridines," J. Org. Chem., vol. 40, No. 16, pp. 2341–2347 (1975).

Pfleiderer, "Synthese und Oxidationsverhalten von 7,8-Dihydroxanthopterinen," Chem. Ber. 107, pp. 785–795 (1974).

Primary Examiner—Mukund J. Shah
Assistant Examiner—Matthew V. Grumbling
Attorney, Agent, or Firm—Finnegan, Henderson, Farabow, Garrett & Dunner

[57] ABSTRACT

Compounds of the formula I

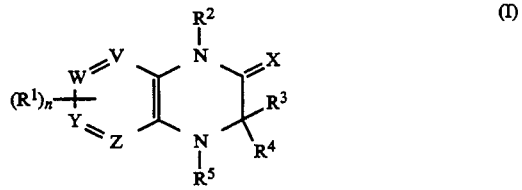

and their tautomeric form of the formula Ia

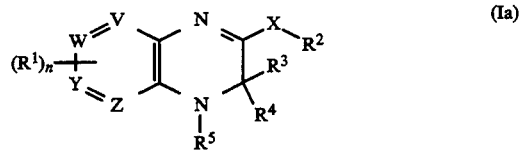

in which the substituents $R^1$ to $R^5$ and V, W, Y and Z have the stated meanings, display an effect against viruses.

4 Claims, No Drawings

AZAQUINOXALINES AND THEIR USE

The present invention relates to azaquinoxalines, processes for their preparation and their use.

The basic frameworks of the pteridines and pyridopyrazines have been known for a long time (D. J. Brown, Fused Pyrimidines Vol. III: Pteridines in The Chemistry of Heterocyclic Compounds, E. C. Taylor and A. Weissberger, Eds., John Wiley & Sons, Inc. 1988; G. W. H. Cheeseman, R. F. Cookson, Condensed Pyrazines in The Chemistry of Heterocyclic Compounds, E. C. Taylor and A. Weissberger, Eds., John Wiley & Sons, Inc. 1979). But little is to be found about pyrazinopyridazines in the literature (R. N. Castle, Condensed Pyridazines Including Cinnolines and Phthalazines in The Chemistry of Heterocyclic Compounds, E. C. Taylor and A. Weissberger, Eds., John Wiley & Sons, Inc. 1973).

The unsaturated derivatives xanthopterin and isoxanthopterin are among the most important naturally occurring pteridines. Their antitumor activity stimulated a number of synthetic studies (for example E. C. Taylor, R. F. Abdulla, K. Tanaka and P. A. Jacobi J. Org. Chem. 1975, 40, 2341; W. Pfleiderer Chem. Ber. 1974, 107, 785).

Tetrahydro-2-oxo-8-aminopyrido[2,3-b]pyrazine-7-carboxylic acids are described in a patent application by Squibb & Sons, Inc. as antiinflammatory compounds and as sedatives (US 4077-955, 17.2.1977). A patent application by Ferrosan A/S describes 3-substituted 4,5-dihydro-5-isopropyl-4-oxoimidazo[1,5-a]quinoxalines and -6-azaquinoxalines with strong affinity for the benzodiazepine receptor (EP 320-136-A, 8.12.1987). N-Carboxymethyl-pyrido[2,3-b]pyrido-2(1H)-ones are, inter alia, claimed as aldose reductase inhibitors in a patent application by Carpibem SA (EP 162-776-A, 18.5.1984).

It has now been found, surprisingly, that certain azaquinoxalines have an antiviral activity. The invention accordingly relates to compounds of the formula I

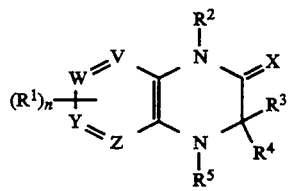

and their tautomeric form of the formula Ia

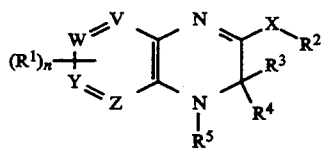

in which n is zero, one, two or three, the individual $R^1$ substituents are, independently of one another, fluorine, chlorine, bromine, iodine, trifluoromethyl, trifluoromethoxy, hydroxyl, mercapto, alkyl, cycloalkyl, alkoxy, alkoxyalkoxy, alkylthio, alkylsulfinyl, alkylsulfonyl, alkylamino, where the alkyl groups can be substituted by fluorine, chlorine, hydroxyl, amino, alkoxy, alkylamino, dialkylamino, acyloxy, acylamino, carboxyl, aminocarbonyl, alkyloxycarbonyl; nitro, amino, azido, dialkylamino, piperidino, piperazino, N-methylpiperazino, morpholino, 1-pyrrolidinyl, acyl, acyloxy, acylamino, cyano, carbamoyl, carboxyl, alkyloxycarbonyl, hydroxysulfonyl, sulfamoyl, or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl or heteroaryl radical which is unsubstituted or substituted by up to five $R^6$ radicals which are independent of one another, where $R^6$ can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, V, W, Y and Z are CH, $CR^1$ or N, where the ring contains a minimum of one and a maximum of two nitrogen atoms, X is oxygen, sulfur, selenium or substituted nitrogen N—$R^2$, in which $R^2$ can have the meanings given below, $R^2$ and $R^5$ can be identical or different and be independently of one another hydrogen, hydroxyl, alkyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkynyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkyl)-(alkyl) optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl) optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkylcarbonyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenylcarbonyl optionally substituted by fluorine, chlorine or hydroxyl, alkoxy, oxo, phenyl;

(cycloalkyl)carbonyl optionally substituted by fluorine, chlorine or hydroxyl, alkoxy, oxo, phenyl;

(cycloalkenyl)carbonyl optionally substituted by fluorine, chlorine or hydroxyl, alkoxy, oxo, phenyl;

(cycloalkyl)-(alkyl)carbonyl optionally substituted by fluorine, chlorine or hydroxyl, alkoxy, oxo, phenyl;

(cycloalkenyl)-(alkyl)carbonyl optionally substituted by fluorine, chlorine or hydroxyl, alkoxy, oxo, phenyl;

alkyloxycarbonyl optionally substituted by fluorine, chlorine, bromine, hydroxyl, alkoxy, alkylamino, dialkylamino, alkylthio;

alkenyloxycarbonyl optionally substituted by fluorine, chlorine, hydroxyl, alkoxy, oxo, phenyl;

alkynyloxycarbonyl optionally substituted by fluorine, chlorine, hydroxyl, alkoxy, oxo, phenyl;

alkylthiocarbonyl optionally substituted by fluorine, chlorine, hydroxyl, alkoxy, oxo, phenyl;

alkenylthiocarbonyl optionally substituted by fluorine, chlorine, hydroxyl, alkoxy, oxo, phenyl; alkylamino- and dialkylaminocarbonyl optionally substituted by fluorine, chlorine, hydroxyl, alkoxy, oxo, phenyl;

alkenylamino- and dialkenylaminocarbonyl optionally substituted by fluorine, chlorine, hydroxyl, alkoxy, oxo, phenyl;

alkylsulfonyl optionally substituted by fluorine, chlorine, hydroxyl, alkoxy, alkylthio, oxo, phenyl;

alkenylsulfonyl optionally substituted by fluorine, chlorine, hydroxyl, alkoxy, oxo, phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl, arylalkoxycarbonyl which is substituted by up to five $R^6$ radicals which are independent of one another, where $R^6$ is as defined above, or heteroaryl, heteroarylalkyl, heteroarylalkenyl, heteroarylalkylcarbonyl or heteroarylalkenylcarbonyl which is substituted by up to three $R^6$ radicals which are independent of one another, $R^3$ and $R^4$ can be identical or different and be independently of one another hydrogen, alkyl optionally substituted by fluorine, chlorine, hydroxyl, amino, mercapto, acyloxy, benzoyloxy, acylamino, benzyloxy, phenoxy, alkoxy, alkylamino, dialkylamino, alkylthio, alkylsulfonyl, alkylsulfinyl, carboxyl, alkyloxycarbonyl, aminocarbonyl, carbamoyl;

alkenyl optionally substituted by fluorine or chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl optionally substituted by fluorine or chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl; or aryl, arylalkyl, heteroaryl or heteroarylalkyl which is substituted by up to five $R^6$ radicals which are independent of one another, where $R^6$ is as defined above, with the exception of the compounds in which $R^2$ and $R^5$ and/or $R^3$ and $R^4$ are simultaneously hydrogen.

Preferred compounds of the abovementioned formula I or Ia are those in which:

2) n is zero, one or two, the individual $R^1$ substituents are, independently of one another, fluorine, chlorine, bromine, trifluoromethyl, trifluoromethoxy, hydroxyl, mercapto, $C_1$–$C_6$-alkyl, $C_5$–$C_6$-cycloalkyl, $C_1$–$C_4$-alkoxy, ($C_1$–$C_4$-alkoxy)-($C_1$–$C_2$-alkoxy), $C_1$–$C_4$-alkylthio, $C_1$–$C_4$-alkylsulfinyl, $C_1$–$C_4$-alkylsulfonyl, $C_1$–$C_4$-alkylamino, where the alkyl groups can be substituted by fluorine, chlorine, hydroxyl, amino, carboxyl, aminocarbonyl, $C_1$–$C_4$-alkyloxycarbonyl;

amino, di($C_1$–$C_4$-alkyl)amino, $C_1$–$C_4$-acyl, $C_1$–$C_4$-acyloxy, $C_1$–$C_4$-acylamino, cyano, carbamoyl, carboxyl, ($C_1$–$C_4$-alkyl)-oxycarbonyl or a phenyl, phenoxy, benzoyl, heteroaroyl or heteroaryl radical which is substituted by an $R^6$ radical, where $R^6$ can be fluorine, chlorine, trifluoromethyl, $C_1$–$C_4$-alkyl, $C_3$–$C_6$-cycloalkyl, $C_1$–$C_4$-alkoxy, V, W, Y and Z are CH, $CR^1$ or N, where the ring contains a minimum of one and a maximum of two nitrogen atoms, X is oxygen, sulfur or substituted nitrogen N—$R^2$ in which $R^2$ can have the meanings given below, $R^2$ and $R^5$ can be identical or different and be independently of one another hydrogen, hydroxyl, $C_1$–$C_6$-alkyl, $C_2$–$C_6$-alkenyl, $C_3$–$C_6$-alkynyl, $C_3$–$C_6$-cycloalkyl, $C_5$–$C_6$-cycloalkenyl, ($C_3$–$C_6$-cycloalkyl)-($C_1$–$C_2$-alkyl), ($C_5$–$C_6$-cycloalkenyl)-($C_1$–$C_2$-alkyl), $C_1$–$C_6$-alkylcarbonyl, $C_2$–$C_6$-alkenylcarbonyl, ($C_3$–$C_6$-cycloalkyl)carbonyl, ($C_5$–$C_6$-cycloalkenyl)carbonyl, ($C_3$–$C_6$-cycloalkyl)-($C_1$–$C_2$-alkyl)carbonyl, ($C_5$–$C_6$-cycloalkenyl)-($C_1$–$C_2$-alkyl)carbonyl, $C_1$–$C_6$-alkyloxycarbonyl, $C_2$–$C_6$-alkenyloxycarbonyl, optionally substituted by fluorine, chlorine, phenyl, hydroxyl;

$C_2$–$C_6$-alkynyloxycarbonyl optionally substituted by fluorine, chlorine, phenyl;

$C_1$–$C_6$-alkylthiocarbonyl, $C_2$–$C_6$-alkenylthiocarbonyl, $C_1$–$C_6$-alkylamino-and di($C_1$–$C_6$-alkyl)aminocarbonyl, $C_2$–$C_6$-alkenylaminocarbonyl, di($C_1$–$C_6$-alkenyl)aminocarbonyl, $C_1$–$C_6$-alkylsulfonyl, $C_2$–$C_6$-alkenylsulfonyl;

or aryl, arylalkyl, arylalkenyl, arylalkynyl, arylalkylcarbonyl, arylalkenylcarbonyl, arylalkoxycarbonyl which is substituted by an $R^6$ radical, where the alkyl, alkenyl or alkynyl radical can in each case contain 1 to 3 carbon atoms and $R^6$ is as defined above, or heteroaryl, heteroarylalkyl, heteroarylalkenyl, heteroarylalkylcarbonyl or heteroarylalkenylcarbonyl which is substituted by up to two $R^6$ radicals which are independent of one another, where the alkyl or alkenyl radical can in each case contain 1 to 3 carbon atoms, $R^3$ and $R^4$ can be identical or different and be independently of one another hydrogen, $C_1$–$C_6$-alkyl optionally substituted by hydroxyl, amino, mercapto, $C_1$–$C_4$-alkoxy, $C_1$–$C_4$-alkylamino, di($C_1$–$C_4$-alkyl)amino, $C_1$–$C_4$-alkylthio, $C_1$–$C_4$-alkylsulfonyl, $C_1$–$C_4$-alkylsulfinyl, carboxyl, $C_1$–$C_4$-alkyloxycarbonyl or aminocarbonyl;

$C_2$–$C_6$-alkenyl, $C_3$–$C_6$-cycloalkyl, $C_3$–$C_6$-cycloalkenyl, aryl, arylalkyl, heteroaryl or heteroarylalkyl which is substituted by up to two $R^6$ radicals which are independent of one another, where the alkyl radical can in each case contain 1 to 3 carbon atoms, and $R^6$ is as defined above, with the exception of the compounds in which $R^2$ and $R^5$ and/or $R^3$ and $R^4$ are simultaneously hydrogen.

Particularly preferred compounds of the abovementioned formula I or Ia are those in which:

3) n is zero, one or two, the individual $R^1$ substituents are, independently of one another, fluorine, chlorine, bromine, trifluoromethyl, trifluoromethoxy, hydroxyl, mercapto, $C_1$–$C_6$-alkyl, $C_1$–$C_4$-alkoxy, $C_1$–$C_4$-alkylthio, amino, $C_1$–$C_4$-alkylamino, di($C_1$–$C_4$-alkyl)amino ($C_1$–$C_2$-alkyl)oxycarbonyl($C_1$–$C_4$-alkyl)amino, $C_1$–$C_6$-acyl, $C_1$–$C_4$-acylamino, or a phenyl radical which is substituted by an $R^6$ radical, where $R^6$ can be fluorine, chlorine, trifluoromethyl, $C_1$–$C_4$-alkyl, $C_1$–$C_4$-alkoxy, V, W, Y and Z are CH, $CR^1$ or N, where the ring contains a minimum of one and a maximum of two nitrogen atoms, X is oxygen or sulfur, $R^2$ and $R^5$ can be identical or different and be independently of one another hydrogen, hydroxyl, $C_1$–$C_6$-alkyl, $C_2$–$C_6$-alkenyl, $C_3$–$C_6$-alkynyl, $C_1$–$C_6$-alkyloxycarbonyl, $C_2$–$C_6$-alkenyloxycarbonyl, $C_1$–$C_6$-alkylthicarbonyl, $C_2$–$C_6$-alkenylthiocarbonyl, $C_1$–$C_6$-alkylsulfonyl, $C_2$–$C_6$-alkenylsulfonyl;

or arylalkyl, arylalkenyl which is substituted by an $R^6$ radical, where the alkyl or alkenyl radical can in each case contain 1 to 3 carbon atoms, and $R^6$ is as defined above, or heteroarylalkyl which is substituted by up to two $R^6$ radicals which are independent of one another, where the alkyl radical can in each case contain 1 to 3 carbon atoms, $R^3$ and $R^4$ can be identical or different and be independently of one another hydrogen, $C_1$–$C_6$-alkyl optionally substituted by hydroxyl, amino, mercapto, $C_1$–$C_4$-alkoxy, $C_1$–$C_4$-alkylthio, $C_1$–$C_4$-alkylsulfonyl, $C_1$–$C_4$-alkylsulfinyl or carboxyl; $C_2$–$C_6$-alkenyl, phenyl or benzyl which is substituted by up to two $R^6$ radicals which are independent of one another, where $R^6$ is as defined above, with the exception of the compounds in which $R^2$ and $R^5$ and/or $R^3$ and $R^4$ are simultaneously hydrogen.

Very particularly preferred compounds of the formula I or Ia are those in which:

4) n is zero or one, the individual $R^1$ substituents are, independently of one another, fluorine, chlorine, trifluoromethyl, hydroxyl, mercapto, $C_1$–$C_3$-alkyl, $C_1$–$C_3$-alkoxy, $C_1$–$C_3$-alkylthio, amino, $C_1$–$C_3$-alkylamino, di($C_1$–$C_3$-alkyl)amino, ($C_1$–$C_2$-alkyl)oxycarbonyl($C_1$–$C_4$-alkyl)amino, $C_1$–$C_3$-acylamino, V, W, Y and Z are CH, $CR^1$ or N, where the ring contains a minimum of one and a maximum of two nitrogen atoms, X is oxygen or sulfur, $R^2$ and $R^5$ can be identical or different and be independently of one another hydrogen, hydroxyl, $C_1$–$C_3$-alkyl, $C_2$–$C_6$-alkenyl, $C_1$–$C_4$-alkyloxycarbonyl, $C_2$–$C_4$-alkenyloxycarbonyl, or a 2-, 3- or 4-picolyl radical, $R^3$ and $R^4$ can be identical or different and be independently of one another hydrogen, $C_1$–$C_4$-alkyl optionally substituted by $C_1$–$C_2$-alkylthio, $C_1$–$C_2$-alkylsulfonyl or $C_1$–$C_2$-alkylsulfinyl;

with the exception of the compounds in which $R^2$ and $R^5$ or $R^3$ and $R^4$ are simultaneously hydrogen.

Particularly preferred basic elements of the abovementioned compounds of the formulae I and Ia are 3,4-dihydro-1,4,5-triazanaphthalen-2(1H)-one or -thione, 3,4-dihydro-1,4,6-triazanaphthalen-2(1H)-one or -thione, 1,2-dihydro-1,4,6-triazanaphthalen-3(4H)-one or -thione, 3,4-dihydro-1,4,5,7-tetraazanaphthalen-2(1H)-one or -thione.

1,2-dihydro-1,4,5,7-tetraazanaphthalen-3(4H)-one or -thione.

The alkyl groups mentioned in the foregoing definitions can be straight-chain or branched. Unless otherwise defined, they preferably contain 1–8, particularly preferably 1–6, especially 1–4 carbon atoms. Examples are the methyl, ethyl, propyl, 1-methylethyl, butyl, 1-methylpropyl, 2-methylpropyl, 1,1-dimethylethyl group and the like.

The alkenyl groups mentioned in the foregoing definitions can be straight-chain or branched and contain 1 to 3 double bonds. Unless otherwise defined, these groups preferably contain 2–8, in particular 2–6 carbon atoms. Examples are the 2-propenyl, 1-methylethenyl, 2-butenyl, 3-butenyl, 2-methyl-2-propenyl, 3-methyl-2-butenyl, 2,3-dimethyl-2-butenyl, 3,3-dichloro-2-propenyl and pentadienyl group and the like.

The alkynyl groups mentioned in the foregoing definitions can be straight-chain or branched and contain 1 to 3 triple bonds. Unless otherwise defined, they preferably contain 2–8, particularly preferably 3–6 carbon atoms. Examples are the 2-propynyl and 3-butynyl group and the like.

The cycloalkyl and cycloalkenyl groups mentioned in the foregoing definitions contain, unless otherwise defined, preferably 3–8, particularly preferably 4–6 carbon atoms. Examples are the cyclopropyl, cyclobutyl, cyclopentyl, cyclopentenyl, cyclohexyl or cyclohexenyl group.

The acyl groups mentioned in the foregoing definitions can be aliphatic, cycloaliphatic or aromatic. Unless otherwise defined, they preferably contain 1–8, particularly preferably 2–7 carbon atoms. Examples of acyl groups are the formyl, acetyl, chloroacetyl, trifluoroacetyl, hydroxyacetyl, glycyl, propionyl, butyryl, isobutyryl, pivaloyl, cyclohexanecarbonyl or benzoyl group.

The aryl groups mentioned in the foregoing definitions are preferably aromatic groups with 6–14 carbon atoms, in particular with 6–10 carbon atoms such as, for example, phenyl and naphthyl.

Examples of particularly suitable hetero atoms in the abovementioned heterocyclic rings or heteroaryl groups are O, S, N, with N—Z being present in the case of an N-containing ring saturated at this point, in which Z is H or $R^2$ with the definitions described in each case above.

Unless otherwise defined, the heterocyclic rings preferably have 1–15 carbon atoms and 1–6 hetero atoms, especially 3–11 carbon atoms and 1–4 hetero atoms.

Suitable examples for the heterocyclic rings or hetero-aryl groups mentioned in the foregoing definitions are thiophene, furan, pyridine, pyrimidine, indole, quinoline, isoquinoline, oxazole, isoxazole, thiazole or isothiazole.

The aralkyl groups listed in the foregoing definitions are, for example, benzyl, phenylethyl, naphthylmethyl or styryl.

The abovementioned $R^1$ to $R^6$ substituents are preferably substituted 3 times, particularly preferably twice, in particular once, by the substituents indicated in each case.

The ranges for the individual substituents which have been described previously as preferred are likewise preferred for the particular combinations of substituent definitions (such as, for example, arylalkoxycarbonyl).

Depending on the various substituents, compounds of the formulae I and Ia may have a plurality of asymmetric carbon atoms. The invention therefore relates both to the pure stereoisomers and to mixtures thereof such as, for example, the relevant racemate. The pure stereoisomers of the compounds of the formulae I and Ia (Ib and Ic) can be prepared directly, or subsequently separated, by known methods or in analogy to known methods.

The present invention furthermore relates to a process for preparing compounds of the formula I and Ia as explained above under 1)–4), which comprises A) for preparing compounds of the formula I with X equal to oxygen and the radicals $R^1$, $R^2$, $R^3$, $R^4$, $R^5$ and n as defined under 1) to 4), reacting a compound of the formula II

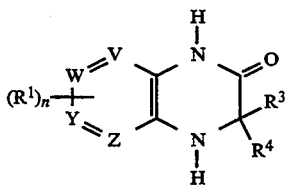

(II)

where the definitions mentioned under 1) to 4) apply to $R^1$, $R^3$ and $R^4$, with a compound of the formula III

R—L$^1$ (III)

where R has the meanings mentioned above under 1) to 4) for $R^5$ and $R^2$ with the exception of hydrogen, hydroxyl, alkoxy, aryloxy, acyloxy, amino, alkylamino, dialkylamino, arylamino, acylamino, and $L^1$ is a leaving group, or comprises B) preparing compounds of the formula I with X equal to sulfur and the radicals $R^1$, $R^2$, $R^3$, $R^4$ and $R^5$ as defined under 1) to 4) by reacting a compound of the formula I where X is oxygen, and the definitions described under 1) to 4) apply to $R^1$ to $R^5$ with a sulfurization reagent, or comprises C) preparing compounds of the formula Ia where X and the radicals $R^1$ to $R^5$ are defined as under 1) to 4) by reacting a compound of the formula IV

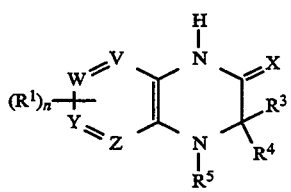

(IV)

or IVa

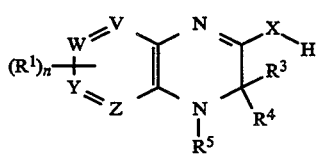

(IVa)

where the definitions mentioned under 1) to 4) apply to X, $R^1$, $R^3$, $R^4$ and $R^5$, with a compound of the formula III

R—L$^1$ (III)

where R has the meanings mentioned above under 1) to 4) for $R^2$ with the exception of hydrogen, hydroxyl, alkoxy, aryloxy, acyloxy, amino, alkylamino, dialkylamino, arylamino, acylamino, and Z is a leaving group, or comprises D) preparing compounds of the formula I with X equal to oxygen and the radicals $R^1$ to $R^5$ as defined under 1) to 4) by cyclizing a compound of the formula V

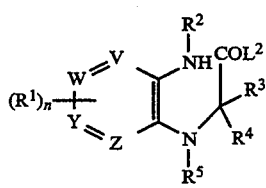

(V)

with $R^1$ to $R^5$ as defined under 1) to 4), and $L^2$ equal to hydroxyl, alkoxy, optionally halogenated acyloxy, chlorine, bromine or iodine, or comprises E) preparing compounds of the formula I where X is equal to oxygen, $R^4$ and $R^5$ are hydrogen, and the definitions mentioned under 1) to 4) apply to $R^1$ to $R^3$, from the azaquinoxalinones of the formula XI

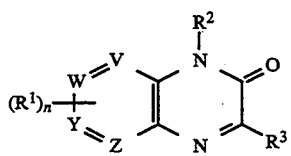

(XI)

with $R^1$ to $R^3$ as defined under 1) to 4), by addition of hydrogen onto the C≡N bond, or comprises F) preparing compounds of the formula I where X equals oxygen and $R^1$ to $R^5$ are defined as under 1) to 4), from compounds of the formula VI

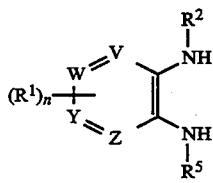

(VI)

with $R^1$, $R^2$ and $R^5$ as defined under 1) to 4), by reaction with chloroform or bromoform and a carbonyl compound of the formula XIII

R$^3$—CO—R$^4$ (XIII)

with $R^3$ and $R^4$ as defined under 1) to 4), or with α-(trihalogenomethyl)alkanols of the formula XIV Hal$_3$C—C(OH)—R$^3$R$^4$ (XIV)

in which Hal is Cl, Br or I, and in which $R^3$ and $R^4$ are defined as under 1) to 4), or comprises G) preparing compounds of the formula I with X equal to oxygen, $R^1$, $R^2$, $R^3$ and $R^4$ as defined under 1) to 4) and $R^5$ C$_1$–C$_8$-alkyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_3$-$C_8$-alkenyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_3$-$C_8$-alkynyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_4$-$C_8$-cycloalkyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_5$-$C_8$-cycloalkenyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

($C_1$-$C_6$-alkoxy)-($C_1$-$C_6$-alkyl), di($C_1$-$C_6$-alkylamino)-($C_1$-$C_6$-alkyl), ($C_3$-$C_6$-cycloalkyl)alkyl, ($C_6$-$C_8$-cycloalkenyl)alkyl, arylalkyl, naphthylalkyl or heteroarylalkyl which is substituted by up to five $R^6$ radicals which are independent of one another, where the alkyl radical can in each case contain 1 to 3 carbon atoms, by reductive alkylation of a compound of the formula I where $R^5$ is hydrogen and X is oxygen, and the definitions mentioned under 1) to 4) apply to $R^1$, $R^2$, $R^3$ and $R^4$, with a carbonyl compound of the formula XV

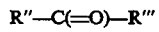

$$R''\text{—}C(\text{=}O)\text{—}R''' \qquad (XV)$$

where R" and R'" can be identical or different and be independently of one another hydrogen, $C_1$-$C_7$-alkyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_3$-$C_7$-alkenyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_3$-$C_7$-alkynyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_4$-$C_8$-cycloalkyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

$C_5$-$C_8$-cycloalkenyl optionally substituted by fluorine, chlorine, bromine, iodine, phenyl, mercapto, hydroxyl, $C_1$-$C_6$-acyloxy, benzoyloxy, phenoxy, $C_1$-$C_6$-alkoxy, $C_1$-$C_6$-alkylamino, di($C_1$-$C_6$-alkyl)amino, $C_1$-$C_6$-alkylthio, cyano, carboxyl, carbamoyl;

($C_1$-$C_6$-alkoxy)-($C_1$-$C_5$-alkyl), di($C_1$-$C_6$-alkylamino)-($C_1$-$C_5$-alkyl), ($C_3$-$C_6$-cycloalkyl)alkyl, ($C_6$-$C_8$-cycloalkenyl)alkyl, arylalkyl, naphthylalkyl or heteroarylalkyl which is substituted by up to five $R^6$ radicals which are independent of one another, where the alkyl radical can in each case contain 0 to 2 carbon atoms, and where R" and R'" can be linked together to form a 4- to 8-membered ring.

The abovementioned method A) is preferably carried out under the following conditions:

The substituent $L^1$ in the formula III is a suitable leaving group such as, for example, chlorine, bromine or iodine, a suitable radical of sulfuric acid, an aliphatic or aromatic sulfonic ester or optionally halogenated acyloxy.

The reaction is expediently carried out in an inert solvent. Suitable examples are aromatic hydrocarbons such as toluene or xylene, lower alcohols such as methanol, ethanol or 1-butanol, ethers such as tetrahydrofuran or glycol dimethyl ether, dipolar aprotic solvents such as N,N-dimethylformamide, N-methyl-2-pyrrolidone, acetonitrile, nitrobenzene, dimethyl sulfoxide or mixtures of these solvents.

Two-phase systems with aqueous solutions of bases in the presence of a phase-transfer catalyst such as, for example, benzyltriethylammonium chloride are also possible.

The presence of a suitable base, for example of an alkali metal or alkaline earth metal carbonate or bicarbonate such as sodium carbonate, calcium carbonate or sodium bicarbonate, of an alkali metal or alkaline earth metal hydroxide such as potassium hydroxide or barium hydroxide, of an alcoholate such as sodium ethanolate or potassium tert-butylate, of an organolithium compound such as butyllithium or lithium diisopropylamide, of an alkali metal or alkaline earth metal hydride such as sodium hydride or calcium hydride, an alkali metal fluoride such as potassium fluoride or of an organic base such as triethylamine or pyridine to trap the acid liberated in the reaction may be beneficial. In some cases it is appropriate to add an iodine salt, for example potassium iodide. The reaction is usually carried out at temperatures between $-10°$ and $160°$ C., preferably at room temperature.

For this reaction it is necessary for any nucleophilic substituents such as, for example, hydroxyl, mercapto or amino groups, with the exception of position 1 and/or 4 in compounds of the formula II or in III, to be derivatized in a suitable way or provided with conventional protective groups which can be eliminated again, such as, for example, acetyl or benzyl, before carrying out the reaction.

The sulfurization reagent preferably used for the reaction as described previously under B) is 2,4-bis(4-methoxyphenyl)-1,3-dithia-2,4-diphosphetane 2,4-disulfide (Lawesson's reagent), bis(tricyclohexyltin) sulfide, bis(tri-n-butyltin) sulfide, bis(triphenyltin) sulfide, bis(trimethylsilyl) sulfide or phosphorus pentasulfide.

The reaction is expediently carried out in an inert organic solvent such as, for example, carbon disulfide, toluene or xylene, at room temperature or above, preferably at the boiling point of the reaction mixture, and where possible under anhydrous conditions. When the tin or silyl sulfides mentioned are used it is appropriate to carry out the sulfurization reaction in the presence of a Lewis acid such as boron trichloride.

In the presence of other carbonyl groups in a compound of the formula I, for example in a compound where X equals oxygen and one or more $R^1$ to $R^6$ radicals equal acyl, the carbonyl must be protected before the sulfurization reaction in accordance with known methods by a suitable protective group, for example by acetalization; subsequent elimination of protective groups leads to the desired compound.

$L^1$ for the reaction described above under C) is a suitable leaving group, preferably chlorine, bromine or iodine, a suitable radical of sulfuric acid, an aliphatic or aromatic sulfonic ester or optionally halogenated acyloxy.

The reaction conditions for this reaction correspond to those in method A.

The cyclization described under D) takes place in a suitable solvent such as, for example, methanol, ethanol, N,N-dimethylformamide or N-methylpyrrolidone in the presence of a base; alkali metal or alkaline earth metal carbonates or bicarbonates such as sodium carbonate, calcium carbonate or sodium bicarbonate, alkali metal or alkaline earth metal hydroxides such as potassium hydroxide or barium hydroxide, alcoholates such as sodium ethanolate or potassium tert-butylate, organolithium compounds such as butyllithium or lithium diisopropylamide, alkali metal or alkaline earth metal hydrides such as sodium hydride or calcium hydride or an organic base such as triethylamine or pyridine—the latter can also be used as solvents, or organic or inorganic acids such as glacial acetic acid, trifluoroacetic acid, hydrochloric acid or phosphoric acid are suitable. The reaction is preferably carried out at temperatures between 20° and 120° C., particularly preferably at room temperature.

The compounds of the formula V where $R^1$ to $R^5$ and $L^2$ are defined as under 1) to 4) or D) can be obtained from compounds of the formula VI

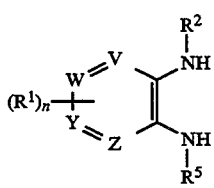
(VI)

where $R^1$, $R^2$ and $R^5$ are defined as under 1) to 4), by alkylation with a compound of the formula VII

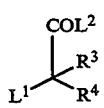
(VII)

where $R^3$, $R^4$ and $L^2$ are defined as under 1) to 4) or D) and $L^1$ is defined as under A). The reaction conditions for this alkylation correspond to those given for method A).

Under suitable conditions there is simultaneous ring closure to give the azadihydroquinoxaline of the formula I.

Compounds of the formula V in which $R^1$, $R^3$ to $R^5$ and $L^2$ are defined as under 1) to 4) or D), and $R^2$ is hydrogen, can also be prepared from compounds of the formula VIII

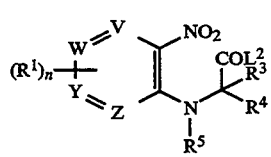
(VIII)

with $R^1$, $R^3$ to $R^5$ and Y as defined under 1) to 4) or D), by reducing the nitro group to the amino group by known processes.

Under suitable conditions, for example on reduction in the presence of acid, there is simultaneous ring closure to give the azadihydroquinoxaline of the formula I.

The reduction is carried out by standard methods (see, for example, Methoden der organischen Chemie (Methods of Organic Chemistry) (Houben-Weyl), E. Müller (editor); G. Thieme Verlag, Stuttgart 1957; Vol. XI/1, pp. 360–490) for example with tin(II) chloride in glacial acetic acid, $TiCl_3$ in hydrochloric acid, or by catalytic hydrogenation, with the choice of the reagent being determined by the chemical stability of the various $R^1$, $R^3$ to $R^5$ substituents; if, for example, one of the radicals is alkenyl, the first method will be chosen in order to retain the double bond.

The ortho-diaminopyridines, -pyridazines and -pyrimidines required as starting materials for the syntheses described are known from the literature or can be bought or can be synthesized by methods known from the literature.

N-Ortho-nitropyridyl-, N-ortho-nitropyridazyl- and N-ortho-nitropyrimidyl-amino acid derivatives of the formula VIII where $R^1$ and $R^3$ to $R^5$ are defined as under 1) to 4), and $L^2$ is equal to $OR^7$, with $R^7$ equal to hydrogen, alkyl, or phenyl, benzyl or 9-fluorenylmethyl which are optionally in each case substituted by, for example, halogen, can be obtained by, for example, amination of ortho-halogenonitropyridines or -pyrimidines of the formula IX

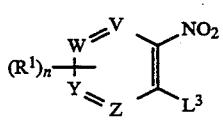
(IX)

where $R^1$ is as defined under 1) to 4), and $L^3$ is fluorine, chlorine, bromine or iodine, with amino acids or their esters of the formula X

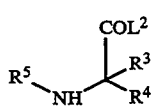
(X)

where $R^3$, $R^4$, $R^5$ and $L^2$ are as defined under 1) to 4) or above.

The reaction can be carried out in the presence of an inorganic or organic auxiliary base such as, for example, sodium or potassium carbonate, sodium hydroxide or triethylamine. It is beneficial to use an inert solvent at temperatures between 0° and 150° C., preferably at the reflux temperature. Suitable solvents are open-chain or cyclic ethers, for example tetrahydrofuran or glycol dimethyl ether, aromatic hydrocarbons, for example toluene or chlorobenzene, alcohols, for example ethanol, isopropanol or glycol monomethyl ether, dipolar aprotic solvents, for example N,N-dimethylformamide, N-methylpyrrolidone or 1,3-dimethyl-tetrahydro-2(1H)-pyrimidone.

The N-ortho-nitrophenylamino acids of the formula VIII with $L^2$ equal to hydroxyl can, if desired or necessary, be converted by well-known standard methods into the acid derivatives of the formula VIII with $L^2$ equal to alkoxy, optionally halogenated acyloxy, chlorine, bromine or iodine.

Ortho-halogenonitropyridines and -pyrimidines of the formula IX and amino acids of the formula X are known from the literature and can be bought or can be prepared by methods known from the literature.

The reaction described above under E) preferably takes place by catalytic hydrogenation (with hydrogen) or hydrosilylation (with alkylsilanes, for example diphenylsilane) in the presence of a hydrogenation catalyst, for example Raney nickel or palladium on carbon, under a hydrogen pressure of 1 to 5 bar or using a reducing agent from the class of complex metal hydrides such as sodium borohydride or sodium cyanoborohydride or using metals or metal salts and acid such as, for example, zinc/glacial acetic acid or $SnCl_2$/HCl. The reaction is expediently carried out in an inert solvent such as lower alcohols, for example methanol or isopropanol, ethers such as tetrahydrofuran or glycol dimethyl ether, dipolar aprotic solvents such as N,N-dimethylformamide, aromatic hydrocarbons such as toluene or xylene or mixtures of these solvents at temperatures between $-20°$ and $100°$ C., preferably at room temperature.

In the presence of substituents in compounds of the formula XI which may be hydrogenated or reduced under the described conditions, for example oxo, it is necessary to use an intermediate of the formula XI with substituents which are not attacked but which can be derivatized to give the required group, for example hydroxyl. The substituents can also be provided with a conventional protective group, for example an acetal protective group, which can be removed again after the reaction described above.

Azoquinoxalines of the formula XI with $R^1$ to $R^3$ as defined under 1) to 4) can be obtained in accordance with known processes by condensation of an ortho-amine of the formula VI where $R^1$ and $R^2$ are defined as under 1) to 4), and $R^5$ is equal to hydrogen, with an alpha-keto carboxylic acid of the formula XII $$R^3\text{---}CO\text{---}COOR^8 \qquad (XII)$$

where $R^3$ is defined as under 1) to 4), and $R^8$ is hydrogen or alkyl.

The reaction is expediently carried out in an inert solvent in a temperature range between $0°$ and $150°$ C.; examples of suitable solvents are alcohols, for example ethanol or 2-methoxyethanol, open-chain or cyclic ethers, for example glycol dimethyl ether or tetrahydrofuran, or dipolar aprotic solvents, for example N,N-dimethylformamide or acetonitrile.

The reaction described above under F) is expediently carried out in a two-phase system composed of an organic, water-immiscible solvent or solvent mixture composed, for example, of halogenated hydrocarbons, for example dichloromethane or 1,2-dichloroethane, or aromatic hydrocarbons, for example toluene or xylene, and a concentrated aqueous solution of an alkali metal or alkaline earth metal hydroxide, for example sodium or barium hydroxide. The presence of a phase-transfer catalyst is advantageous, such as, for example, benzyltriethylammonium chloride or tetrabutylammonium bromide.

The reaction is usually carried out at temperatures between $0°$ and $50°$ C., preferably at room temperature Substituents in compounds of the formulae VI and XIII, or XIV, which are unstable under the reaction conditions must be replaced by those which can be derivatized to the required group. The substituents can also be provided with a conventional protective group which can be removed again after the reaction described above.

The reaction described under G) preferably takes place by catalytic hydrogenation (with hydrogen) in the presence of a hydrogenation catalyst, for example palladium on carbon, under a hydrogen pressure of 1 to 5 bar, or using a reducing agent from the class of complex metal hydrides such as sodium borohydride, sodium triacetoxyborohydride or sodium cyanoborohydride. The reaction is expediently carried out in an inert solvent such as lower alcohols, for example methanol or isopropanol, ethers, for example tetrahydrofuran or glycol dimethyl ether, halogenated hydrocarbons, for example dichloromethane or 1,2-dichloroethane, at temperatures between $-20°$ and $100°$ C., preferably at room temperature. The presence of an acid, such as, for example, acetic acid or trifluoroacetic acid, or of a Lewis acid, such as, for example, titanium tetrachloride, is advantageous. In the presence of substituents in compounds of the formulae I and XV which may be hydrogenated or reduced under the conditions described, for example oxo, it is necessary to use an intermediate of the formulae I and XV with substituents which are not attacked but which can be derivatized to give the required group, for example hydroxyl. Acid-labile groups such as, for example, acetals, or groups which react under the reaction conditions, such as, for example, primary amines, should likewise be avoided or be provided with a conventional protective group.

The present invention also relates to pharmaceuticals with a content of at least one compound according to the invention. The present invention additionally relates to the use of compounds of the formula I

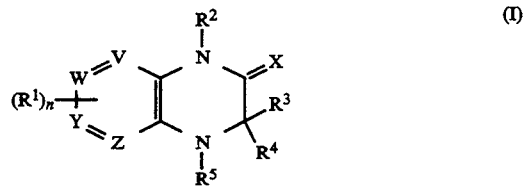

and their tautomeric form of the formula Ia

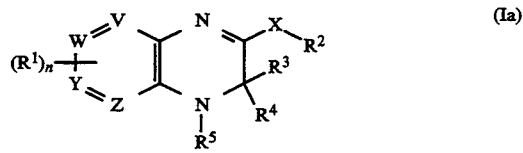

in which
1) n is zero, one, two or three,
the individual $R^1$ substituents are, independently of one another,
fluorine, chlorine, bromine, iodine, trifluoromethyl, trifluoromethoxy, hydroxyl, mercapto, alkyl, cycloalkyl, alkoxy, alkoxyalkoxy, alkylthio, alkylsulfinyl, alkylsulfonyl, alkylamino, where the alkyl groups can be substituted by fluorine, chlorine, hydroxyl, amino, alkoxy, alkylamino, dialkylamino, acyloxy, acylamino, carboxyl, aminocarbonyl, alkyloxycarbonyl;
nitro, amino, azido, dialkylamino, piperidino, piperazino, N-methylpiperazino, morpholino, 1-pyrrolidinyl, acyl, acyloxy, acylamino, cyano, carbamoyl, carboxyl, alkyloxycarbonyl, hydroxysulfonyl, sulfamoyl, a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl or heteroaryl radical which is unsubstituted or substituted by up to five $R^6$ radicals which are independent of one another, where $R^6$ can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, V, W, Y and Z are CH, $CR^1$ or N, where the ring contains a minimum of one and a maximum of two nitrogen atoms, X is oxygen, sulfur, selenium or substituted nitrogen N—$R^2$ in which $R^2$ can have the meaning given below, $R^2$ and $R^5$ can be identical or different and be independently of one another hydrogen, hydroxyl, alkyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkynyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

cycloalkenyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkyl)-(alkyl) optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

(cycloalkenyl)-(alkyl) optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkylcarbonyl optionally substituted by fluorine, chlorine, bromine, iodine, phenyl, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl, carbamoyl;

alkenylcarbonyl optionally substituted by fluorine, chlorine or hydroxyl, alkoxy, oxo, phenyl;

(cycloalkyl)carbonyl optionally substituted by fluorine, chlorine or hydroxyl, alkoxy, oxo, phenyl;

(cycloalkenyl) carbonyl optionally substituted by fluorine, chlorine or hydroxyl, alkoxy, oxo, phenyl;

(cycloalkyl)-(alkyl) carbonyl optionally substituted by fluorine, chlorine or hydroxyl, alkoxy, oxo, phenyl;

(cycloalkenyl)-(alkyl)carbonyl optionally substituted by fluorine, chlorine or hydroxyl, alkoxy, oxo, phenyl;

alkyloxycarbonyl optionally substituted by fluorine, chlorine, bromine, hydroxyl, alkoxy, alkylamino, dialkylamino, alkylthio;

alkenyloxycarbonyl optionally substituted by fluorine, chlorine, hydroxyl, alkoxy, oxo, phenyl;

alkynyloxycarbonyl optionally substituted by fluorine, chlorine, hydroxyl, alkoxy, oxo, phenyl;

alkylthiocarbonyl optionally substituted by fluorine, chlorine, hydroxyl, alkoxy, oxo, phenyl;

alkenylthiocarbonyl optionally substituted by fluorine, chlorine, hydroxyl, alkoxy, oxo, phenyl;

alkylamino- and dialkylaminocarbonyl optionally substituted by fluorine, chlorine, hydroxyl, alkoxy, oxo, phenyl;

alkenylamino- and dialkenylaminocarbonyl optionally substituted by fluorine, chlorine, hydroxyl, alkoxy, oxo, phenyl;

alkylsulfonyl optionally substituted by fluorine, chlorine, hydroxyl, alkoxy, alkylthio, oxo, phenyl;

alkenylsulfonyl optionally substituted by fluorine, chlorine, hydroxyl, alkoxy, oxo, phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl, arylalkoxycarbonyl which is substituted by up to five $R^6$ radicals which are independent of one another, where $R^6$ is as defined above, or heteroaryl, heteroarylalkyl, heteroarylalkenyl, heteroarylalkylcarbonyl or heteroarylalkenylcarbonyl which is substituted by up to three $R^6$ radicals which are independent of one another, $R^3$ and $R^4$ are identical or different and are independently of one another hydrogen, alkyl optionally substituted by fluorine, chlorine, hydroxyl, amino, mercapto, acyloxy, benzoyloxy, acylamino, benzyloxy, phenoxy, alkoxy, alkylamino, dialkylamino, alkylthio, alkylsulfonyl, alkylsulfinyl, carboxyl, alkyloxycarbonyl, aminocarbonyl, carbamoyl;

alkenyl optionally substituted by fluorine or chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkyl optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl;

cycloalkenyl optionally substituted by fluorine or chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl, carbamoyl; or aryl, arylalkyl, heteroaryl or heteroarylalkyl which is substituted by up to five $R^6$ radicals which are independent of one another, where $R^6$ is as defined above, $R^3$ and $R^4$ or $R^3$ and $R^5$ can furthermore also be part of a saturated or unsaturated carbocyclic or heterocyclic ring which is optionally substituted by fluorine, chlorine, hydroxyl, amino, alkyl, alkenyl, alkynyl, acyloxy, benzoyloxy, alkoxy, alkylthio, oxo, thioxo, carboxyl, carbamoyl or phenyl, where the heterocyclic ring contains O, S or N as hereto atom and where N—$R^2$ or N—H is present in the case of an N-containing ring saturated at this point, in which $R^2$ is as defined above, for the production of pharmaceuticals for the treatment of viral diseases, especially for the treatment of diseases caused by human immunodeficiency virus (HIV).

The pharmaceuticals according to the invention can be used enterally (orally), parenterally (intravenously), rectally, subcutaneously, intramuscularly or locally (topically).

They can be administered in the form of solutions, powders, tablets, capsules (including microcapsules), ointments (creams or gels) or suppositories. Suitable auxiliary substances for formulations of these types are the pharmaceutically customary liquid or solid fillers and extenders, solvents, emulsifiers, lubricants, flavorings, colorants and/or buffer substances.

0.1–30, preferably 0.2–10, mg/kg of body weight are administered one or more times a day as expedient dosage. The dosage units used expediently depend on the particular pharmacokinetics of the substance used and on the pharmaceutical formulation used.

The dosage unit which is used of the compounds according to the invention is, for example, 1–1500 mg, preferably 50–500 mg.

The compounds according to the invention can also be administered in combination with other antiviral agents such as, for example, nucleoside analogs, protease inhibitors or adsorption inhibitors and immunostimulants, interferons, interleukins and colony-stimulating factors (for example GM-CSF, G-CSF, M-CSF).

Activity tests

Tests on products against HIV in cell culture

Description of methods

Medium:
RPMI pH 6.8 Complete medium additionally contains 20% fetal calf serum and 40 IU/ml recombinant interleukin 2.

Cells:
Lymphocytes isolated from fresh donor blood by means of ®Ficoll gradient centrifugation are cultivated in complete medium with the addition of 2 µg/ml phytohemagglutinin (Wellcome) at 37° C. under 5% $CO_2$ for 36 h. The cells are, after addition of 10% DMSO, frozen at a cell density of $5 \times 10^6$ and stored in liquid nitrogen. For the test, the cells are thawed, washed in RPMI medium and cultivated in complete medium for 3–4 days.

Mixture:
The test products were dissolved in DMSO and adjusted with complete medium to a concentration of 1 mg/ml. 0.4 ml of medium was placed in 24-well dishes. After addition of 0.1 ml of the dissolved product to the upper row of the dish, a geometric dilution series was produced by transferring 0.1 ml each time. Product-free controls always received 0.4 ml of complete medium with 0.5% DMSO. Lymphocyte cultures with a cell count of $5 \times 10^5$ cells/ml were infected by adding 1/50 of the volume of supernatant from HIV-infected lymphocyte cultures. The titer of these culture supernatants was determined by endpoint dilution to be $1-5 \times 10^6$ infectious units/ml. After incubation at 37° C. for 30 min, the infected lymphocytes were spun down and taken up again in the same volume of medium. 0.6 ml portions of this cell suspension were placed in all the wells of the assay plate. The mixtures were incubated at 37° C. for 3 days.

Evaluation:

The infected cell cultures were examined under the microscope for the presence of giant cells which indicate active virus replication in the culture. The lowest product concentration at which no giant cells occurred was determined as the HIV inhibitory concentration. As a control, the supernatants from the culture plates were examined for the presence of HIV antigen with the aid of an HIV antigen assay in accordance with the information from the manufacturer (Organon).

Results:
The results of this assay are shown in Table 1.

TABLE 1

| Compound of Example No. | T-cell culture assay MIC (µg/ml) |
|---|---|
| 2 | >0.8 |
| 8 | 0.08 |
| 10 | 1.0 |
| 11 | 0.2 |
| 37 | >1.0 |
| 41 | >2.0 |

Investigation of the substances for inhibition of HIV reverse transcriptase

The reverse transcriptase (RT) activity was determined by means of a scintillation proximity assay (SPA). The reagent kit for the RT-SPA was purchased from Amersham/Buchler (Braunschweig). The RT enzyme (cloned from HIV in *E. coli*) originated from HT-Biotechnology LTD, Cambridge, UK.

Mixture:
The assay was carried out according to the method manual of the manufacturer Amersham—with the following modifications:

Bovine serum albumin was added to the final concentration of 0.5 mg/ml to the assay buffer.

The assay was carried out in Eppendorf reaction vessels with a volume of 100 µl of mixture.

The RT concentrate from the manufacturer (5000 U/ml) was diluted to an activity of 15 U/ml in tris-HCl buffer 20 mM; pH 7.2; 30% glycerol.

The incubation time for the mixtures was 60 min (37° C.).

After stopping the reaction and "developing" with the bead suspension, 130 µl of mixture were transferred into 4.5 ml of tris-HCl buffer, 10 mM; pH 7.4; 0.15 M NaCl and the tritium activity was measured in a β-counter.

Tests on substances:
For a preliminary test of the inhibitory activity, the substances were dissolved in DMSO (stock solution c=1 mg/ml) and tested diluted $10^{-1}$, $10^{-2}$, $10^{-3}$ etc. in DMSO.

To determine $IC_{50}$ values, the inhibitor stock solutions were further diluted in tris-HCl buffer, 50 mM, pH 8 and tested in suitable concentrations.

The concentration appertaining to 50% enzyme inhibition was found from the graph of RT activity against the logarithm of the concentration of the particular test substance.

The results of the investigation are shown in Table 2.

TABLE 2

| Compound of Example No. | Reverse transcriptase assay $IC_{50}$ (µg/ml) |
|---|---|
| 2 | 1–10 |
| 8 | 0.1–1 |

TABLE 2-continued

| Compound of Example No. | Reverse transcriptase assay IC$_{50}$ (μg/ml) |
| --- | --- |
| 10 | 0.1–1 |
| 11 | 0.1–1 |
| 20 | 1–10 |
| 37 | 0.1–1 |

The present invention is explained in more detail by the following examples and by the contents of the patent claims.

EXAMPLE 1

(3RS)-3-Methyl-3,4-dihydro-1,4,6-triazanaphthalen-2(1H)- one

3-Methyl-1,4,6-triazanaphthalen-2(1H)-one (J. W. Clark-Lewis, R. P. Singh J. Chem. Soc. 1962, 3162) (3.1 g, 0.02 mol) was hydrogenated in 300 ml of methanol with palladium catalysis (10% Pd/carbon) under 1 atm of hydrogen. After hydrogen uptake ceased, the catalyst was filtered off with suction, the solvent was removed, and the residue was stirred with diethyl ether and filtered off with suction. 2.6 g (82%) of the desired product of melting point 230° C. (dec.) were obtained.

$^1$H-NMR (200 MHz, DMSO-d$_6$): δ=1.27 (d, J=7 Hz, 3H), 3.87 (dd, J=7.2 Hz, 1H), 6.24 (br. s, 1H), 6.69 (d, J=5 Hz, 1H), 7.75 (d, J=5 Hz, 1H), 7.92 (s, 1H), 10.53 ppm (br. s, 1H). MS: (M+H)$^+$=164

EXAMPLE 2

(3S)-6-Chloro-3-methyl-3,4-dihydro-1,4,5-triazanaphthalen-2(1H)-one

N-(6-Chloro-3-nitro-2-pyridyl)-alanine methyl ester (A) and N-[6-(1-(methoxycarbonyl)ethylamino)-3-nitro-2-pyridyl]alanine methyl ester (B)

L-Alanine methyl ester hydrochloride (8.4 g, 0.06 mol) was dissolved in 100 ml of anhydrous N,N-dimethylformamide, and 16.6 ml (0.12 mol) of triethylamine were added. Subsequently, while stirring vigorously, 10.7 g (0.05 mol) of 2,6-dichloro-3-nitropyridine in 20 ml of anhydrous N,N-dimethylformamide were slowly added dropwise, during which the reaction temperature rose above 40° C. After a further 3 h at room temperature, the reaction mixture was poured into about 400 ml of ice-water, extracted three times with ethyl acetate, dried (sodium sulfate) and concentrated. After chromatography on silica gel (ethyl acetate/heptane=1:5 then 1:2), 9.0 g (69%) of compound A were isolated as a yellow oil, $^1$H-NMR (200 MHz, DMSO-d$_6$): δ=1.51 (d, J=7 HZ, 3H), 3.69 (s, 3H), 4.73 (quint., J=7 Hz, 1H), 6.89 (d, J=8.5 Hz, 1H), 8.48 (d, J=8.5 Hz, 1H), 8.67 ppm (d, J=7 Hz, 1H). MS: (M+H)$^+$=260

A more polar fraction comprised 2.4 g (15%) of compound B as a yellow solid of melting point 113°-114° C.

$^1$H-NMR (200 MHz, DMSO-d$_6$): δ=1.35–1.45 (m, 6H), 3.65 (s, 3H), 3.69 (s, 3H), 4.46 (quint., J=7 Hz, 1H), 4.65 (quint., J=7 Hz, 1H), 6.09 (d, J=9.5 Hz, 1H), 8.05 (d, J=9.5 Hz, 1H), 8.48 (d, J=7 Hz, 1H) 8.96 ppm (d, J=7 Hz, 1H). MS: (M+H)$^+$=327

Compound A (9.0 g, 0.05 mol) was dissolved in 200 ml of methanol and hydrogenated with Raney nickel catalysis under 1 atm of hydrogen. After hydrogen uptake ceased, the catalyst was filtered off with suction, and the solvent was removed in vacuo. The solid product was stirred with diethyl ether, resulting in 2.4 g of pure product (melting point 236°-237° C.).

The residue from the mother liquor was dissolved in 150 ml of hot glacial acetic acid and left to stand at room temperature, when precipitation occurred. Concentration, stirring with saturated aqueous sodium bicarbonate solution and filtration with suction resulted in 4.9 g of melting point 235°-236° C. Recrystallization from isopropanol resulted in 2.4 g of the desired product of melting point 239°-240° C.

$^1$H-NMR (200 MHz, DMSO-d$_6$): δ=1.43 (d, J=7.5 Hz, 3H), 4.06 (q, J=7.5 Hz, 1H), 6.59 (d, J=7.5 Hz, 1H), 6.95 (d, J=7.5 Hz, 1H), 7.33 (br. s, 1H), 10.45 ppm (br. s, 1H). MS: (M+H)$^+$=198

EXAMPLE 3

(2RS)-1-(Isopropenyloxycarbonyl)-2-methyl-1,2-dihydro-1,4,6-triazanaphthalen-3(4H)-one (2RS)-2-Methyl-1,2-dihydro-1,4,6-triazanaphthalen-3(4H)-one (A. Albert, G. B. Barlin J. Chem. Soc. 1963, 5156) (570 mg, 3.5 mmol) was dissolved in 30 ml of anhydrous pyridine and cooled in an ice bath. 0.42 ml (3.8 mmol) of isopropenyl chloroformate was added dropwise, and the mixture was subsequently stirred at room temperature overnight. Concentration, chromatography on silica gel (ethyl acetate/methanol=20:1) and crystallization (pentane/diethyl ether) resulted in 100 mg (12%) of the desired product of melting point 170°-171° C.

$^1$H-NMR (200 MHz, DMSO-d$_6$): δ=1.20 (d, J=7.5 Hz, 3H), 1.98 (s, 3H), 4.75–4.90 (m, 3H), 7.65 (d, J=6 Hz, 1H), 8.19 (d, J=6 Hz, 1H), 8.23 (s, 1H), 10.96 ppm (br. s, 1H). MS: (M+H)$^+$=248

EXAMPLE 4

(2RS)-1,4-Bis(isopropenyloxycarbonyl)-2-methyl-1,2-dihydro-1,4,6-triazanaphthalen-3(4H)-one (2RS)-2-Methyl-1,2-dihydro-1,4,6-triazanaphthalen-3(4H)-one (A. Albert, G. B. Barlin J. Chem. Soc. 1963, 5156) (570 mg, 3.5 mmol) was suspended in 80 ml of anhydrous dichloromethane, and a solution of 408 mg (3.5 mmol) of sodium carbonate was added. While stirring vigorously, 0.42 ml (3.8 mmol) of isopropenyl chloroformate was added dropwise, and the mixture was subsequently stirred at room temperature for 5 h. After addition of saturated aqueous sodium chloride solution, the phases were separated, the aqueous was back-extracted twice with dichloromethane, and the combined organic phases were dried (sodium sulfate) and concentrated. Chromatography on silica gel (ethyl acetate/heptane=1:1) resulted in 420 mg of the product as a pale oil, which crystallized from pentane/diethyl ether; yield 300 mg (35%) of melting point 96°-97° C.

$^1$H-NMR (200 MHz, DMSO-d$_6$): δ=1.20 (d, J=7.5 Hz, 3H), 1.99 (s, 3H), 2.03 (s, 3H), 4.87 (d, J=7.5 Hz, 2H), 4.96 (q, J=7.5 Hz, 1H), 7.70 (d, J=6 Hz, 1H), 8.41 (d, J=6 Hz, 1H), 8.63 ppm (s, 1H). MS: (M+H)$^+$=332

EXAMPLE 5

(3RS)-4-(Isopropenyloxycarbonyl)-3-methyl-3,4-dihydro-1,4,6-triazanaphthalen-2(1H)-one The desired compound, of melting point 236° C., was obtained from the compound of Example 1 as described for Example 3.

$^1$H-NMR (200 MHz, DMSO-d$_6$): δ=1.20 (d, J=7 Hz, 3H), 1.95 (s, 3H), 4.6–5.0 (m, 3H), 6.97 (d, J=6 Hz, 1H), 8.23 (d, J=6 Hz, 1H), 8.72 (br. s, 1H), 11.11 ppm (br. s, 1H). MS: (M+H)+=248, (M−(CH$_3$)$_2$CO+H)+=190

EXAMPLE 6 AND EXAMPLE 7

(2RS)-2-Methyl-1-(3-methyl-2-butenyl)-1,2-dihydro-1,4,6-triazanaphthalen-3(4H)-one hydrobromide (Example 6) and
2(RS)-2-methyl-1,4-bis(3-methyl-2-butenyl)-1,2-dihydro-1,4,6-triazanaphthalen-3(4H)-one hydrobromide (Example 7)

(2RS)-2-Methyl-1,2-dihydro-1,4,6-triazanaphthalen-3(4H)-one (A. Albert, G. B. Barlin J. Chem. Soc. 1963, 5156) (570 mg, 3.5 mmol) was dissolved in 20 ml of anhydrous N,N-dimethylformamide and, after addition of 445 mg (4.2 mmol) of sodium carbonate and 0.49 ml (4.2 mmol) of 3-methyl-2-butenyl bromide, was stirred at room temperature for 4 h. The reaction solution was concentrated in vacuo and chromatographed on silica gel (dichloromethane/methanol=9:1). The compound of Example 7 was obtained as less polar fraction, 170 mg of melting point 110°–115° C.

$^1$H-NMR (200 MHz, DMSO-d$_6$): δ=1.42 (d, J=7 Hz, 3H), 1.69 (s, 3H), 1.76 (s, 6H), 1.78 (s, 3H), 4.4–4.55 (m, 3H), 4.83 (m, 2H), 5.06 (m, 1H), 5.38 (m, 1H), 6.90 (d, J=6 Hz, 1H), 7.80 (s, 1H), 8.06 (d, J=6 Hz, 1H), 9.20 ppm (br. s, 1H). MS: (M+H)+=300

The more polar fraction contained the compound of Example 6, 630 mg of melting point 203° C.

$^1$H-NMR (200 MHz, DMSO-d$_6$): δ=1.42 (d, J=7 Hz, 3H), 1.75–1.8 (m, 6H), 4.38 (q, J=7 Hz, 1H), 4.79 (d, J=8 Hz, 2H), 5.35 (m, 1H), 6.83 (d, J=7.5 Hz, 1H), 7.68 (d, J=2 Hz, 1H), 8.00 (dd, J=7.5, 2 Hz, 1H), 9.08 (br. s, 1H), 10.93 ppm (br. s, 1H). MS: (M+H)+=232

EXAMPLE 8

(3S)-6-Chloro-3-methyl-4-(3-methyl-2-butenyl)-3,4-dihydro-1,4,5-triazanaphthalen-2(1H)-one The compound of Example 2 (988 mg, 5.0 mmol) was suspended in 40 ml of anhydrous 1,2-dichloroethane. While stirring, 840 mg (10 mmol) of 3,3-dimethylacrolein and subsequently 1.9 ml (25 mmol) of trifluoroacetic acid were added. The mixture was cooled in an ice bath, 2.1 g (10 mmol) of sodium triacetoxyborohydride were introduced in portions, and the mixture was stirred at 0° C. for 1 h and at room temperature for a further 3 h. The reaction mixture was then added to about 150 ml of saturated aqueous sodium bicarbonate solution, the phases were separated, the aqueous was back-extracted three times with dichloromethane, and the combined organic extracts were dried (sodium sulfate) and concentrated. Chromatography on silica gel (ethyl acetate/heptane=1:2) provided 650 mg (49%) of the desired compound as a crystalline solid of melting point 136°–137° C.

$^1$H-NMR (200 MHz, DMSO-d$_6$): δ=1.24 (d, J=7 Hz, 3H), 1.71 (s, 6H), 3.74 (dd, J=15, 9 Hz, 1H), 4.05 (q, J=7 Hz, 1H), 4.37 (dd, J=15, 6 Hz, 1H), 5.23 (m, 1H), 6.65 (d, J=8 Hz, 1H), 6.98 (d, J=8 Hz, 1H), 10.61 ppm (s, 1H). MS: (M+H)+=266

EXAMPLE 9

(3S)-6-Chloro-1-(isopropenyloxycarbonyl)-3-methyl-3,4-dihydro-1,4,5-triazanaphthalen-2(1H)-one The compound of Example 2 (988 mg, 5.0 mmol) was dissolved in 30 ml of anhydrous pyridine. After addition of 0.6 ml (5.5 mmol) of isopropenyl chloroformate, the mixture was stirred at room temperature for 4 h and subsequently concentrated. The residue was dissolved in ethyl acetate and washed three times with water, dried (sodium sulfate) and concentrated. After chromatography on silica gel (ethyl acetate/heptane=1:2), the desired compound was isolated and crystallized from diethyl ether/pentane; yield 380 mg (27%) of melting point 86°–87° C.

$^1$H-NMR (200 MHz, DMSO-d$_6$): δ=1.35 (d, J=6 Hz, 3H), 2.0 (s, 3H), 4.16 (q, J=6 Hz, 1H), 4.95 (s, 2H), 6.82 (d, J=9 Hz, 1H), 7.45 (d, J=9 Hz, 1H), 7.60 ppm (br. s, 1H). MS (M+H)+=282

EXAMPLE 10

(3S)-6-Chloro-1,4-his(isopropenyloxycarbonyl)-3-methyl-3,4-dihydro-1,4,5-triazanaphthalen-2(1H)-one The compound of Example 2 (988 mg, 5.0 mmol) was dissolved in 80 ml of anhydrous dichloromethane, and 593 mg (7.5 mmol) of anhydrous pyridine were added. At 0° C., 663 mg (5.5 mmol) of isopropenyl chloroformate were added dropwise. The mixture was subsequently left to stir at room temperature for 3 d. It was washed three times with water, dried (sodium sulfate) and concentrated. After chromatography on silica gel (acetone/heptane=1:4), 360 mg (25%) of the product were isolated as an oil.

$^1$H-NMR (270 MHz, DMSO-d$_6$): δ=1.20 (d, J=7.5 Hz, 3H), 1.98 (s, 3H), 2.01 (s, 3H), 4.81 (s, 2H), 4.97 (s, 2H), 5.04 (q, J=7.5 Hz, 1H), 7.49 (d, J=8 Hz, 1H), 8.02 ppm (d, J=8 Hz, 1H). MS (M+H)+=366

EXAMPLE 11 AND EXAMPLE 12

(3S)-6-Chloro-3-methyl-4-(2-picolyl)-3,4-dihydro-1,4,5-triazanaphthalen-2(1H)-one (Example 11) and
(3S)-6-chloro-1-hydroxy-3-methyl-4-(2-picolyl)-3,4-dihydro-1,4,5-triazanaphthalen-2(1H)-one (Example 12)

2,6-Dichloro-3-nitropyridine (4.3 g, 0.02 mol) in 50 ml of 1,2-dimethoxyethane and 3.3 ml (0.024 mol) of triethylamine were heated under reflux with 3.9 g (0.02 mol) of N-(2-picolyl)-alanine methyl ester for 4 h. The mixture was then concentrated, taken up in ethyl acetate and washed twice with water. After drying (sodium sulfate) and concentrating, 6.9 g of N-(6-chloro-3-nitro-2-pyridyl)-N-(2-picolyl)alanine methyl ester remained as a brown oil which was employed directly for the hydrogenation. A solution in 100 ml of methanol was hydrogenated with Raney nickel catalysis under 1 atm of hydrogen. After hydrogen uptake ceased, the catalyst was filtered off with suction, and the filtrate was concentrated and chromatographed on silica gel (ethyl acetate/methanol=20:1). 720 mg (12%) of the compound of Example 11, of melting point 185° C., were eluted as the less polar fraction.

$^1$H-NMR (200 MHz, DMSO-d$_6$): δ=1.27 (d, J=6.5 Hz, 3H), 4.11 (q, J=6.5 Hz, 1H), 4.43 (d, J=16 Hz, 1H), 5.15 (d, J=16 Hz, 1H), 6.69 (d, J=7.5 Hz, 1H), 7.03 (d, J=7.5 Hz, 1H), 7.2–7.4 (m, 2H), 7.75 (dt, J=8, 2.5 Hz, 1H), 8.53 (m, 1H), 10.68 ppm (s, 1H). MS (M+H)+=289

1.75 g (29%) of the compound of Example 12, of melting point 183° C., were eluted as the more polar fraction.

$^1$H-NMR (200 MHz, DMSO-d$_6$): δ=1.31 (d, J=7 Hz, 3H), 4.33 (q, J=7 Hz, 1H), 4.45 (d, J=16 Hz, 1H), 5.15 (d, J=16 Hz, 1H), 6.77 (d, J=8 Hz, 1H), 7.2–7.4 (m, 2H), 7.75 (dt, J=7.5, 2 Hz, 1H), 8.52 (m, 1H), 10.92 ppm (s, 1H). MS (M+H)+=305

EXAMPLE 13 AND EXAMPLE 14

(3RS)-3-Methyl-4-(3-methyl-4-butenyl)-3,4-dihydro-1,4,6-triazanaphthalen-2(1H)-one hydrobromide (Example 13) and
(3RS)-3-methyl-1,4-bis(3-methyl-4-butenyl)-3,4-dihydro-1,4,6-triazanaphthalen-2(1H)-one hydrobromide (Example 14)

The compound of Example 1 (570 mg, 3.5 mmol) was dissolved in 20 ml of anhydrous N,N-dimethylformamide and, after addition of 445 mg (4.2 mmol) of sodium carbonate and 0.49 ml (4.2 mmol) of dimethylallyl bromide, stirred at room temperature for 5 h. The mixture was subsequently concentrated in vacuo and chromatographed on silica gel (dichloromethane/methanol=9:1). 160 mg of the compound of Example 14, of melting point 103°–105° C., were isolated as the less polar fraction.

$^1$H-NMR (200 MHz, DMSO-d$_6$): δ=1.35 (d, J=6.5 Hz, 3H), 1.60 (s, 3H), 1.80 (s, 3H), 1.83 (s, 3H), 4.26 (q, J=6.5 Hz, 1H), 4.58 (d, J=7.5 Hz, 2H), 4.95–5.1 (m, 3H), 5.45 (m, 1H), 7.32 (d, J=7 Hz, 1H), 7.48 (br. s, 1H), 8.01 (d, J=2 Hz, 1H), 8.25 ppm (dd, J=7, 2 Hz, 1H). MS: (M+H)$^+$=300

The more polar fraction comprised 300 mg of the compound of Example 13 of melting point 167°–168° C.

$^1$H-NMR (200 MHz, DMSO-d$_6$): δ=1.35 (d, J=6.5 Hz, 3H), 1.79 (br. s, 3H), 1.82 (br. s, 3H), 4.20 (q, J=6.5 Hz, 1H), 4.96 (d, J=7.5 Hz, 2H), 5.41 (m, 1H), 7.12 (d, J=6.5 Hz, 1H), 7.36 (br. s, 1H), 7.94 (br. s, 1H), 8.13 (dd, J=6.5, 2 Hz, 1H), 11.58 ppm (br. s, 1H). MS: (M+H)$^+$=232

EXAMPLE 15

6-Chloro-3,3-dimethyl-3,4-dihydro-1,4,5-triazanaphthalen-2(1H)-one 9.21 g (0.06 mol) of methyl 2-aminoisobutyrate hydrochloride and 16.6 ml (0.12 mol) of triethylamine were dissolved in 100 ml of anhydrous N,N-dimethylformamide, with simultaneous precipitation of triethylamine hydrochloride, and subsequently a solution of 10.7 g (0.05 mol) of 2,6-dichloro-3-nitropyridine in 20 ml of anhydrous N,N-dimethylformamide was added dropwise. Heating at 60° C. for 3 h was followed by pouring into ice-water, extracting three times with ethyl acetate, drying (sodium sulfate) and concentrating.

After chromatography on silica gel (methyl t-butyl ether/heptane=1:9), 5.64 g (41%) of methyl N-(6-chloro-3-nitro-2-pyridyl)-2-aminoisobutyrate of melting point 96°–97° C. were isolated.

$^1$H-NMR (200 MHz, DMSO-d$_6$): δ=1.60 (s, 6H), 3.62 (s, 3H), 6.89 (d, J=9 Hz, 1H), 8.43 (br. s, 1H), 8.47 ppm (d, J=9 Hz, 1H). MS (M+H)$^+$=274

Methyl N-(6-chloro-3-nitro-2-pyridyl)-2-aminoisobutyrate (4.0 g, 14.6 mmol) was hydrogenated in 250 ml of methanol with Raney nickel catalysis under 1 atm of hydrogen. After hydrogen uptake ceased, the catalyst was filtered off with suction, and the filtrate was concentrated and chromatographed on silica gel (ethyl acetate/heptane=1:2). 1.89 g (61%) of the compound of Example 15, of melting point 229° C., were obtained.

$^1$H-NMR (200 MHz, DMSO-d$_6$): δ=1.30 (s, 6H), 6.61 (d, J=8.5 Hz, 1H), 6.95 (d, J=8.5 Hz, 1H), 7.36 (s, 1H), 10.43 ppm (s, 1H). MS (M+H)$^+$=212

EXAMPLE 16

3,3-Dimethyl-6-methoxy-3,4-dihydro-1,4,5-triazanaphthalen-2(1H)-one

Methyl N-(6-chloro-3-nitro-2-pyridyl)-2-aminoisobutyrate (for preparation see under Example 15) (3.0 g, 10.8 mmol) was dissolved in excess sodium methanolate solution in methanol (100 ml) and stirred at room temperature for 3 h. The mixture was subsequently concentrated, taken up in ethyl acetate, washed three times with water, dried (sodium sulfate) and concentrated. Crystallization from methyl t-butyl ether/heptane resulted in 2.14 g (73%) of methyl N-(6-methoxy-3-nitro-2-pyridyl)-2-aminoisobutyrate of melting point 92° C.

$^1$H-NMR (200 MHz, DMSO-d$_6$): δ=1.63 (s, 6H), 3.60 (s, 3H), 3.80 (s, 3H), 6.24 (d, J=9 Hz, 1H), 8.34 (d, J=9 Hz, 1H), 8.73 ppm (br. s, 1H).

Methyl N-(6-methoxy-3-nitro-2-pyridyl)-2-aminoisobutyrate (1.5 g, 5.6 mmol) was hydrogenated as described for Example 15 and yielded, after crystallization from diethyl ether, 770 mg (66%) of the desired compound of melting point 194°–195° C.

MS (M+H)$^+$=208

EXAMPLE 17

(3RS)-3,6-Dimethyl-3,4-dihydro-1,4,5-triazanaphthalen-2(1H)-one 2,3-Diamino-6-methylpyridine (3.0 g, 0.024 mol) and 3.2 ml (0.028 mol) of ethyl pyruvate were heated under reflux in 100 ml of 1,2-dimethoxyethane for 4 h. The resulting precipitate (3.9 g) of 3,6-dimethyl-1,4,5-triazanaphthalen-2(1H)-one was filtered off with suction, dried and used directly for the hydrogenation. A reaction analogous to that described for Example 1 resulted in 2.27 g (58%) of the desired compound of melting point 203°–205° C.

$^1$H-NMR (200 MHz, DMSO-d$_6$): δ=1.28 (d, J=7 Hz, 3H), 2.20 (s, 3H), 3.94 (dq, J=7.2 Hz, 1H), 6.42 (d, J=9 Hz, 1H), 6.72 (br. s, 1H), 6.84 (d, J=9 Hz, 1H), 10.20 ppm (br. s, 1H). MS (M+H)$^+$=178

EXAMPLE 18 AND EXAMPLE 19

(3RS)-4-(Isopropenyloxycarbonyl)-3,6-dimethyl-3,4-dihydro-1,4,5-triazanaphthalen-2(1H)-one (Example 18) and
(3RS)-1,4-bis(isopropenyloxycarbonyl)-3,6-dimethyl-3,4-dihydro-1,4,5-triazanaphthalen-2(1H)-one (Example 19)

The compound of Example 17 (0.75 g, 4.2 mmol) was dissolved in 20 ml of anhydrous dichloromethane, and 4 ml of anhydrous pyridine and 0.72 ml (5.1 mmol) of isopropenyl chloroformate were added. The mixture was stirred at 0° C. for 4 h, washed with 1N aqueous HCl and saturated aqueous sodium chloride solution and dried over sodium sulfate. The solvent was stripped off and then chromatography on silica gel was carried out (ethyl acetate/heptane=1:2). 480 mg (31%) of the compound of Example 19 were isolated as an oil as the less polar fraction.

$^1$H-NMR (200 MHz, DMSO-d$_6$): δ=1.14 (d, J=7 Hz, 3H), 1.95 (s, 3H), 2.01 (s, 3H), 2.45 (s, 3H), 4.75–4.8 (m, 2H), 4.93 (s, 2H), 5.02 (q, J=7.5 Hz, 1H), 7.22 (d, J=8 Hz, 1H), 7.81 ppm (d, J=8 Hz, 1H). MS: (M+H)$^+$=346

The more polar fraction comprised 200 mg (18%) of the compound of Example 18 of melting point 138°–140° C.

$^1$H-NMR (200 MHz, DMSO-d$_6$): δ=1.16 (d, J=7 Hz, 3H), 1.93 (s, 3H), 2.38 (s, 3H), 4.65–4.85 (m, 3H), 7.07 (d, J=8 Hz, 1H), 7.26 (d, J=8 Hz, 1H), 10.71 ppm (s, 1H). MS (M+H)$^+$=262

EXAMPLE 20

(3RS)-4-(Isopropenyloxycarbonyl)-3,6-dimethyl-3,4-dihydro-1,4,5-triazanaphthalene-2(1H)-thione The compound of Example 18 (100 mg, 0.38 mmol) was stirred with 130 mg (0.23 mmol) of Lawesson's reagent in 10 ml of anhydrous toluene at 80° C. for 3 h. The mixture was subsequently concentrated and chromatographed on silica gel (ethyl acetate/heptane=1:1). 40 mg (38%) of the desired compound, of melting point 120°–121° C., were isolated.

$^1$H-NMR (200 MHz, DMSO-d$_6$): δ=1.22 (d, J=7 Hz, 3H), 1.93 (s, 3H), 2.41 (s, 3H), 4.75 (s, 2H), 5.20 (q, J=7 Hz, 1H), 7.14 (d, J=9 Hz, 1H), 7.44 (d, J=9 Hz, 1H), 12.75 ppm (br. s, 1H). MS (M+H)$^+$=278

EXAMPLE 21

(1'S, 3S)-6-[1'-(Methoxycarbonyl)ethylamino]-3-methyl-3,4-dihydro-1,4,5-triazanaphthalen-2(1H)-one 1.63 g (5 mmol) of compound B from Example 2 were hydrogenated in analogy to compound A from Example 2 with Raney nickel catalysis under 1 atm of hydrogen. Working up was followed by chromatography on silica gel (ethyl acetate/acetic acid=150:1). 510 mg (39%) of the desired product, of melting point 191°–192° C., were obtained.

$^1$H-NMR (200 MHz, DMSO-d$_6$): d=1.25 (d, J=7.5 Hz, 3H), 1.32 (d, J=7.5 Hz, 3H), 3.60 (s, 3H), 3.84 (dq, J=2 Hz, J=7.5 Hz, 1H), 4.35 (dq, J=7.5 Hz, J=7.5 Hz, 1H), 5.79 (d, J=7.5 Hz, 1H), 6.19 (s, 1H), 6.26 (d, J=7.5 Hz, 1H), 6.74 (d, J=7.5 Hz, 1H), 9.8 (br s, 1H) MS: (M+B)$^+$=265

EXAMPLE 22

(2RS)-2-Methyl-1,2-dihydro-1,4,5,7-tetraazanaphthalen-3(4H)-one (3RS)-3-Methyl-3,4-dihydro-1,4,5,7-tetraazanaphthalen-2(1H)-one In analogy to Example 17, 3.11 g (28 mmol) of 4,5-diaminopyrimidine were reacted with ethyl pyruvate (reaction conditions: 12 hours at 85° C.). The resulting precipitate was filtered off with suction, dried and hydrogenated directly in analogy to Example 1 with palladium catalysis (10% Pd on carbon). The crude product obtained in this way was chromatographed on silica gel (ethyl acetate/methanol=10:1). There were obtained 3.0 g (65%) of (2RS)-2-methyl-1,2-dihydro-1,4,5,7-tetraazanaphthalen-3(4H)-one of melting point 165° C. and 0.404 g (9%) of (3RS)-3-methyl-3,4-dihydro-1,4,5,7-tetraazanaphthalen-2(1H)-one of melting point >290° C.

(2RS)-2-Methyl-1,2-dihydro-1,4,5,7-tetraazanaphthalen-3(4H)-one $^1$H-NMR (200 MHz, DMSO-d$_6$): d=1.29 (d, J=7 Hz, 3H), 3.98 (dq, J=7 Hz, J=2 Hz, 1H), 6.48 (br s, 1H), 7.95 (s, 1H), 8.16 (s, 1H), 11.1 (br s, 1H) MS: (M+H)$^+$=165

(3RS)-3-Methyl-3,4-dihydro-1,4,5,7-tetraazanaphthalen-2(1H)-one $^1$H-NMR (200 MHz, DMSO-d$_6$): d=1.36 (d, J=7 Hz, 3H), 4.18 (dq, J=7 Hz, J=2 Hz, 1H), 7.68 (s, 1H), 7.81 (s, 1H), 8.08 (s, 1H), 10.45 (s, 1H) MS: (M+B)$^+$=165

(The two structures were assigned by means of NOE NMR experiments on the corresponding carbamates in Examples 23 and 24)

EXAMPLE 23

(3R,S)-4-(Isopropoxycarbonyl)-3-methyl-3,4-dihydro-1,4,5,7-tetraazanaphthalen-2(1H)-one 0.1 g (0.61 mmol) of (3RS)-3-methyl-3,4-dihydro-1,4,5,7-tetraazanaphthalen-2(1H)-one from Example 22 was reacted in analogy to Example 3 with 0.81 ml (0.73 mmol) of isopropyl chloroformate, and the resulting crude product was chromatographed on silica gel (ethyl acetate). 40 mg (26%) of the desired compound, of melting point 155°–156° C., were obtained.

$^1$H-NMR (200 MHz, DMSO-d$_6$): d=1.21 (d, 3 g), 1.25 (d, 3H), 1.30 (d, 3H), 4.75 (q, 1H), 4.98 (hept., 1H), 8.29 (s, 1H), 8.64 (s, 1H), 11.00 (br s, 1H) MS: (M+H)$^+$=251

EXAMPLE 24

(2RS)-1-(Isopropoxycarbonyl)-2-methyl-1,2-dihydro-1,4,5,7-tetraazanaphthalen-3(4H)-one 0.5 g (3.05 mmol) of (2RS)-2-methyl-1,2-dihydro-1,4,5,7-tetraazanaphthalen-3(4H)-one from Example 22 was reacted in analogy to Example 3 with 4.05 ml (3.66 mmol) of isopropyl chloroformate, and the resulting crude product was chromatographed on silica gel (ethyl acetate/heptane=2:1). 250 mg (33%) of the desired compound, of melting point 160°–162° C., were obtained.

$^1$H-NMR (200 MHz, DMSO-$_6$): d=1.23 (d, 3H), 1.28 (d, 3H), 1.33 (d, 3H), 4.88 (q, 1H), 4.98 (hept., 1H), 8.61 (s, 1H), 8.88 (s, 1H), 11.68 (br s, 1H) MS: (M+H)$^+$=251

EXAMPLE 25

(2RS)-1-(Isopropoxycarbonyl)-2-methyl-1,2-dihydro-1,4,5,7-tetraazanaphthalene-3(4H)-thione 100 mg of (2RS)-1-(isopropoxycarbonyl)-2-methyl-1,2-dihydro-1,4,5,7-tetraazanaphthalen-3(4H)-one from Example 24 were reacted with Lawesson's reagent in analogy to Example 20. The crude product after concentration was chromatographed (silica gel; ethyl acetate/heptane=1:1). 30 mg (28%) of the desired compound, of melting point 203°–204° C., were obtained.

$^1$H-NMR (200 MHz, DMSO-d$_6$): d=1.26 (s, 3H), 1.29 (s, 3H), 1.33 (s, 3H), 4.98 (hept., 1H), 5.31 (q, 1H), 8.70 (s, 1H), 8.96 (s, 1H), 13.40 (br s, 1H) MS: (M+H)$^+$=267

EXAMPLE 26

S-3-Methylthiomethyl-3,4-dihydro-1,4,5-triazanaphthalen-2(1H)-one

In analogy to Example 2, but using only one mole equivalent of triethylamine, 5 g (27 mmol) of (-)-S-methyl-L-cysteine methyl ester were reacted with 3.51 g (22.5 mmol) of 2-chloro-3-nitropyridine (reaction conditions: 5 hours at 80° C.). Working up was followed by chromatography on silica gel (n-heptane/acetone/methyl t-butyl ether=5:1:1). 3.3 g (45%) of N-(3-nitro- 2-pyridyl)-(-)-S-methyl-L-cysteine methyl ester, of melting point 95°–97° C., were obtained.

The product was directly reacted further.

3.3 g (12.2 mmol) of N-(3-nitro-2-pyridyl)-(-)-S-methyl-L-cysteine methyl ester were hydrogenated in analogy to Example 15 in methanol with Raney nickel catalysis under 1 atm of hydrogen. Working up and chromatography on silica gel (ethyl acetate/n-heptane=2:1) resulted in 891 mg (35%) of S-3-methylthiomethyl-3,4-dihydro-1,4,5-triazanaphthalen-2(1H)-one of melting point 225°–228° C.

$^1$H-NMR (200 MHz, DMSO-d$_6$): d=2.07 (s, 3H), 2.89 (m, 2H), 4.36 (m, 1H), 6.55 (dd, 1H), 6.78 (br s, 1H), 6.90 (d, 1H), 7.61 (d, 1H), 10.48 (br s, 1H) MS: (M+H)$^+$=210

EXAMPLE 27

3(R,S)-Phenyl-3,4-dihydro-1,4,5-triazanaphthalen-2(1H)-one

In analogy to Example 2, but using only one mole equivalent of triethylamine, 4.45 g (27 mmol) of D/L-phenylglycine methyl ester were reacted with 3.51 g (22 mmol) of 2-chloro-3-nitropyridine. Working up and column chromatography (n-heptane/acetone/methyl t-butyl ether=5:1:1) resulted in 3.27 g (42%) of N-(3-nitro-2-pyridyl)-(D/L)-phenylglycine methyl ester of melting point 70° C.

3.17 g (11 mmol) of N-(3-nitro-2-pyridyl)-(D,L)-phenylglycine methyl ester were hydrogenated with Raney nickel catalysis in analogy to Example 2. Chromatography on silica gel (ethyl acetate/heptane=1:2) resulted in 1.11 g (45%) of 3-(R,S)-phenyl-3,4-dihydro-1,4,5-triazanaphthalen-2(1H)-one of melting point 250° C.

$^1$H-NMR (200 MHz, DMSO-d$_6$): d=5.08 (m, 1H), 6.59 (m, 1H), 6.96 (m, 1H), 7.30 (m, 5H), 7.45 (br s, 1H), 7.68 (m, 1H), 10.55 (br s, 1H) MS: (M+H)$^+$=226

EXAMPLE 28

4-Isopropoxycarbonyl-3-(R,S)-phenyl-3,4-dihydro-1,4,5-triazanaphthalen-2(1H)-one 1,4-Bis(isopropoxycarbonyl)-3-(R,S)-phenyl-3,4-dihydro-1,4,5-triazanaphthalen-2(1H)-one 0.5 g (2 mmol) of 3-(R,S)-phenyl-3,4-dihydro-1,4,5-triazanaphthalen-2(1H)-one (Example 27) were reacted in analogy to Example 3 using isopropyl chloroformate as formyl halide. Working up and chromatography on silica gel (ethyl acetate/n-heptane=1:2) resulted in 0.44 g (70.7%) of 4-isopropoxycarbonyl-3-(R,S)-phenyl-3,4-dihydro-1,4,5-triazanaphthalen-2(1H)-one of melting point 227° C. and 0.1 g (13% ) of 1,4-bis(isopropoxycarbonyl)-3-(R,S)-phenyl-3,4-dihydro-1,4,5-triazanaphthalen-2(1H)-one of melting point 98° C.

4-Isopropoxycarbonyl-3-(R,S)-phenyl-3,4-dihydro-1,4,5-triazanaphthalen-2(1H)-one $^1$H-NMR (200 MHz, DMSO-d$_6$): d=1.23 (d, J=7 Hz, 3H), 1.33 (d, J=7 Hz, 1H), 4.98 (hept., 1H), 5.91 (s, 1H), 7.11–7.37 (m, 7H), 8.08 (m, 1H), 11.07 (br s, 1H) MS: (M+h)$^+$=312

1,4-Bis(isopropoxycarbonyl)-3-(R,S)-phenyl-3,4-dihydro-1,4,5-triazanaphthalen-2(1H)-one $^1$H-NMR (200 MHz, DMSO-d$_6$): d=1.26 (d, 3H), 1.31 (d, 3H), 1.35 (2 d, 6H), 5.01 (hept., 1H), 5.16 (hept., 1H), 6.13 (s, 1H), 7.11–7.38 (m, 6H), 7.66 (m, 1H), 8.25 (m, 1H) MS: (M+H)$^+$=398

EXAMPLE 29

4-Isopropoxycarbonyl-3-(R,S)-phenyl-3,4-dihydro-1,4,5-triazanaphthalene-2(1H)-thione 200 mg (0.64 mmol) of 4-isopropoxycarbonyl-3-(R,S)-phenyl-3,4-dihydro-1,4,5-triazanaphthalen-2(1H)-one were reacted with 400 mg of Lawesson's reagent in analogy to Example 20 (reaction conditions: 10 hours at 80° C. The crude product was concentrated and chromatographed on silica gel (ethyl acetate/n-heptane=1:2). 130 mg (62%) of 4-isopropoxycarbonyl-3-(R,S)-phenyl-3,4-dihydro-1,4,5-triazanaphthalene-2(1H)-thione, of melting point 188°–189° C., were obtained.

$^1$H-NMR (200 MHz, DMSO-d$_6$): d=1.28 (d, J=7 Hz, 3H), 1.31 (d, J=7 Hz, 3H), 5.00 (hept., 1H), 6.38 (s, 1H), 7.18 (m, 1H), 7.25–7.37 (m, 5H), 7.51 (m, 1H), 8.15 (m, 1H), 13.11 (br s, 1H) MS: (M+H)$^+$=328

The compounds of Examples 30 to 46 were obtained by the methods indicated above. The synthesized compounds have the following physical data.

EXAMPLE 30

3,3-Dimethyl-6-methoxy-7-(4-pyridyl)-3,4-dihydro-1,4,5-triazanaphthalen-2(1H)-one Melting point: >270° C. $^1$H-NMR (200 MHz, DMSO-d$_6$): δ=1.33 (s, 6H), 3.83 (S, 3H), 7.15 (br s, 1H), 7.26 (br s, 1H), 7.50 (m, 2H), 8.51 (m, 2H), 10.20 (br s, 1H) MS (M+H)$^+$=285

EXAMPLE 31

3-Phenyl-3,4-dihydro-1,4,5-triazanaphthalen-2(1H)-one

Melting point: 250° C. $^1$H-NMR (200 MHz, DMSO-d$_6$): δ=5.08 (m, 1H), 6.59 (dd, J=5 Hz and 7 Hz, 1H), 6.96 (dd, J=747 and 1 Hz, 1H), 7.30 (m, 5H), 7.45 (br s, 1H), 7.68 (dd, 1H), 10.55 (br s, 1H) MS (M+H)$^+$=226

EXAMPLE 32

6-Chloro-3-methylthiomethyl-3,4-dihydro-1,4,5-triazanaphthalen-2(1H)-one

Melting point: 202°–204° C. $^1$H-NMR (200 MHz, DMSO-d$_6$): δ=2.08 (s, 3H), 2.73–3.05 (m, 2H), 4.43 (m, 1H), 6.53 (d, J=7 Hz, 1H), 6.91 (d, 1H), 8.38 (br s, 1H), 10.62 (br s, 1H) MS (M+H)$^+$=224

EXAMPLE 33

4-Isopropoxycarbonyl-3-methylthiomethyl-3,4-dihydro-1,4,5-triazanaphthalen-2(1H)-one Melting point: 127°–130° C. $^1$H-NMR (200 MHz, DMSO-d$_6$): 67 =1.22 (d, J=7 Hz, 3H), 4.30 (d, J=7 Hz, 3H), 2.05 (s, 3H), 2.49 (dd, J=9 Zr and 8 Hz, 1H), 2.73 (dd, J=5 Hz and 13 Hz, 1H), 4.90 (m, 1H), 7.18 (dd, J=5 Hz and 8 Hz, 1H), 7.33 (dd, J=8 Hz and 1 Hz, 1H), 8.10 (dd, J=5 Hz and 1 Hz, 1H), 10.88 (br s, 1H) MS (M+H)$^+$=296

EXAMPLE 34

6-Chloro-3-phenyl-3,4-dihydro-1,4,5-triazanaphthalen-2(1H)-one

Melting point: 236° C. $^1$H-NMR (200 MHz, DMSO-d$_6$): δ=5.13 (br s, 1H), 6.63 (d, J=8 Hz, 1H), 6.98 (d, J=8 Hz, 1H), 7.23–7.43 (m, 5H), 7.93 (br s, 1H), 10.63 (br s, 1H) MS (M+H)$^+$=260

EXAMPLE 35

6-Chloro-1-isopropoxycarbonyl-3-phenyl-3,4-dihydro-1,4,5-triazanaphthalen-2(1H)-one Melting point: 162°–163° C. $^1$H-NMR (200 MHz, DMSO-d$_6$): δ=1.32 (d, J=7 Hz, 6H), 5.12 (hept., J=7 Hz, 1H), 5.36 (m, 1H), 6.77 (d, J=8 Hz, 1H), 7.20–7.45 (m, 6H), 8.36 (br s, 1H) MS (M+H)$^+$=346

EXAMPLE 36

6-Chloro-4-isopropoxycarbonyl-3-methylthiomethyl-3,4-dihydro-1,4,5-triazanaphthalen-2(1H)-one Melting point: 198°–200° C. $^1$H-NMR (200 MHz, DMSO-d$_6$): δ=1.36 (d, J=7 Hz, 6H), 2.08 (s, 3H), 2.80–3.00 (m, 2H), 4.52 (m, 1H), 5.14 (hept., J=7 Hz, 1H), 6.72 (d, J=9 Hz, 1H), 7.21 (d, J=9 Hz, 1H), 7.64 (br s, 1H) MS (M+H)$^+$=330

EXAMPLE 37

4-Isopropoxycarbonyl-3-methylthiomethyl-3,4-dihydro-1,4,5-triazanaphthalene-2(1H)-thione Melting point: 188°–191° C. $^1$H-NMR (200 MHz, DMSO-d$_6$): δ=1.23 (d, J=7 Hz, 3H), 1.28 (d, J=7 Hz, 3H), 2.08 (s, 3H), 2.46 (dd, J=4 Hz and 14 Hz, 1H), 2.83 (dd, J=4 Hz and 14 Hz, 1H), 4.93 (hept., 1H), 5.31 (dd, J=4 Hz and 12 Hz) 7.25 (dd, J=5 Hz and 8 Hz, 1H), 8.21 (dd, J=1 Hz and 5 Hz, 1H) MS (M+H)$^+$=312

EXAMPLE 38

3-Methylthiomethyl-3-methoxy-3,4-dihydro-1,4,5-triazanaphthalen-2(1H)-one

Melting point: 173°–174° C. $^1$H-NMR (200 MHz, DMSO-d$_6$): 2.08 (s, 3H), 2.86 (m, 2H), 3.71 (s, 3H), 4.29 (m, 1H), 5.95 (d, J=8 Hz, 1H), 6.77 (br s, 1H), 6.93 (d, 1H), 10.25 (br s, 1H) MS (M+H)$^+$=240

EXAMPLE 39

6-Chloro-3-phenyl-1-(isopropenyloxycarbonyl)-3,4-dihydro-1,4,5-triazanaphthalen-2(1H)-one Melting point: 147°–148° C. $^1$H-NMR (200 MHz, DMSO-d$_6$): δ=2.02 (s, 3H), 4.96 (2 s, 2H), 5.37 (d, J=2 Hz, 1H), 6.81 (d, J=8 Hz, 1H), 7.23–7.45 (m, 6H), 8.31 (d, J=2 Hz, 1H) MS (M+H)$^+$=344

EXAMPLE 40

3-Methylsulfinylmethyl-4-isopropoxycarbonyl-3,4-dihydro-1,4,5-triazanaphthalen-2(1H)-one Melting point: 157°–159° C. $^1$H-NMR (200 MHz, DMSO-d$_6$): δ=1.22 (d, J=7 Hz, 3H), 1.28 (d, J=7 Hz, 3H), 2.53 (s, 3H), 2.78–3.13 (m, 2H), 4.92 (hept., J=7 Hz, 1H), 5.20 (m, 1H), 7.22 (m, 1H), 7.36 (m, 1H), 8.13 (m, 1H), 10.95 (br s, 1H) MS (M+H)$^+$=312

EXAMPLE 41

3-Methylsulfonylmethyl-4-isopropoxycarbonyl-3,4-dihydro-1,4,5-triazanaphthalen-2(1H)-one Melting point: 209°–212° C. $^1$H-NMR (200 MHz, DMSO-d$_6$): δ=1.20 (d, J=7 Hz, 3H), 1.28 (d, J=7 Hz, 3H), 2.98 (s, 3H), 3.20–3.48 (m, 2H), 4.92 (hept., 1H), 5.36 (dd, J=4 Hz and 9 Hz, 1H), 7.27 (dd, J=5 Hz and 8 Hz, 1H), 7.39 (dd, J=2 Hz and 8 Hz, 1H), 7.14 (dd, J=5 Hz and 2 Hz), 11.03 (br s, 1H) MS (M+H)$^+$=328

EXAMPLE 42

4-Isopropoxycarbonyl-3-methylthiomethyl-3,4-dihydro-1,4,5-triazanaphthalen-2(1H)-one Melting point: 176° C. $^1$H-NMR (200 MHz, DMSO-d$_6$): 1.20 (d, J=7 Hz, 3H), 1.26 (d, J=1 Hz, 3H), 2.08 (s, 3H), 4.92 (hept. and m overlapping, 2H), 7.11 (dd, J=4 Hz and 8 Hz, 1H), 7.48 (dd, J=8 Hz and 1 Hz, 1H), 7.93 (dd, J=4 Hz and 1 Hz, 1H), 9.61 (br s, 1H), 10.03 (br s, 1H) MS (M+H)$^+$=311

EXAMPLE 43

3-Methyl-6-propylamino-3,4-dihydro-1,4,5-triazanaphthalen-2(1H)-one

Melting point: 190° C. $^1$H-NMR (200 MHz, DMSO-d$_6$): δ=0.90 (t, J=7 Hz, 3H), 1.25 (d, J=7 Hz, 3H), 1.49 (hex., 2H), 3.05 (dt, J=7 Hz, 2H), 3.83 (dq, J=7 Hz and 2 Hz, 1H), 5.71 (d, J=8 Hz, 1H), 5.75 (br s, J=7 Hz, 1H), 6.21 (br s, 1H), 6.73 (d, 1H), 9.78 (br s, 1H) MS: (M+H)$^+$=221

EXAMPLE 44

3-Methyl-6-(4-methyl-1-piperazinyl)-3,4-dihydro-1,4,5-triazanaphthalen-2(1H)-one Melting point: 172° C. $^1$H-NMR (200 MHz, DMSO-d$_6$): δ=1.27 (d, J=7 Hz, 1H), 2.18 (s, 3H), 2.36 (t, J=5 Hz, 4H), 3.30 (t, 4H), 3.88 (dq, J=7 Hz and 2 Hz, 1H), 5.98 (d, J=9 Hz, 1H), 6.43 (br s, 1H), 6.85 (d, 1H), 9.97 (br s, 1H) MS (M+H)$^+$=262

EXAMPLE 45

3-Methyl-6-(N-n-propyl-isopropoxycarbonylamino)-4-isopropylcarbonyl-5-azaquinoxalin-2(1H)-one Melting point: 65° C. $^1$H-NMR (200 MHz, DMSO-d$_6$): δ=0.83 (t, J=7 Hz, 3H), 1.09–1.33 (m, 15H), 1.54 (pent., J=7 Hz, 2H), 3.81 (m, 2H), 4.74–5.05 (m, 3H), 7.36 (br s, 2H), 10.75 (br s, 1H) MS (M+H)$^+$=393

EXAMPLE 46

3-Methyl-6-(isopropoxycarbonylamino)-1,4,5-triazanaphthalen-2(1H)-one

Melting point: foam $^1$H-NMR (200 MHz, DMSO-d$_6$): δ=1.23 (d, J=7 Hz, 6H), 1.28 (d, J=7 Hz, 3H), 3.94 (dq, J=7 Hz and 2 Hz, 1H), 4.85 (hept., 1H), 6.60 (br s, 1H), 6.94 (p5q. 2H), 9.28 (br s, 1H), 10.22 (br s, 1H) MS (M+H)$^+$=265

The following compounds are examples apart from the examples described above:
(2RS)-1-(isopropenyloxycarbonyl)-2-methyl-1,2-dihydro-1,4,6-triazanaphthalene-3(4H)-thione
(3RS)-4-(isopropenyloxycarbonyl)-3-methyl-3,4-dihydro-1,4,6-triazanaphthalene-2(1H)-thione
(2RS)-2-methyl-1-(3-methyl-2-butenyl)-1,2-dihydro-1,4,6-trianaphthalene-3(4H)-thione
(3S)-6-chloro-3-methyl-4-(3-methyl-2-butenyl)-3,4-dihydro-1,4,5-triazanaphthalene-2(1H)-thione 6-chloro-3-methyl-4-(2-picolyl)-3,4-dihydro-1,4,5-triazanaphthalene-2(1H)-thione
6-[1-(methoxycarbonyl)-ethylamino]-3-methyl-4-(2-picolyl)-3,4-dihydro-1,4,5-triazanaphthalen-2(1H)-thione
(3RS)-3-methyl-4-(3-methyl-4-butenyl)-3,4-dihydro-1,4,6-triazanaphthalene-2(1H)-thione
6-chloro-3,3-dimethyl-4-(isopropenyloxycarbonyl)-3,4-dihydro-1,4,5-triazanaphthalen-2(1H)-one 6-chloro-3,3-dimethyl-4-(isopropenyloxycarbonyl)-3,4-dihydro-1,4,5-triazanaphthalene-2(1H)-thione
6-chloro-3,3-dimethyl-4-(2-picolyl)-3,4-dihydro-1,4,5-triazanaphthalen-2(1H)-one
6-chloro-3,3-dimethyl-4-(2-picolyl)-3,4-dihydro-1,4,5-triazanaphthalene-2(1H)-thione
3,3-dimethyl-4-(isopropenyloxycarbonyl)-6-methoxy-3,4-dihydro-1,4,5-triazanaphthalen-2(1H)-one
3,3-dimethyl-4-(isopropenyloxycarbonyl)-6-methoxy-3,4-dihydro-1,4,5-triazanaphthalene-2(1H)-thione
3,3-dimethyl-6-methoxy-4-(2-picolyl)-3,4-dihydro-1,4,5-triazanaphthalen-2(1H)-one
3,3-dimethyl-6-methoxy-4-(2-picolyl)-3,4-dihydro-1,4,5-triazanaphthalene-2(1H)-thione
6-dimethylamino-3,3-dimethyl-6-methoxy-3,4-dihydro-1,4,5-triazanaphthalen-2(1H)-one
3,3-dimethyl-6-methoxy-4-(2-methylthioethyl)-3,4-dihydro-1,4,5-triazanaphthalen-2(1H)-one
3,3-dimethyl-6-methoxy-4-(2-methylthioethyl)-3,4-dihydro-1,4,5-triazanaphthalene-2(1H)-thione
6-chloro-3-methylthiomethyl-3,4-dihydro-1,4,5-triazanaphthalen-2(1H)-one
6-chloro-4-(isopropenyloxycarbonyl)-3-methylthiomethyl-3,4-dihydro-1,4,5-triazanaphthalen-2(1H)-one
6-chloro-4-(isopropenyloxycarbonyl)-3-methylthiomethyl-3,4-dihydro-1,4,5-triazanaphthalene-2(1H)-thione
6-methoxy-3-methylthiomethyl-3,4-dihydro-1,4,5-triazanaphthalen-2(1H)-one
4-(isopropenyloxycarbonyl)-6-methoxy-3-methylthiomethyl-3,4-dihydro-1,4,5-triazanaphthalen-2(1H)-one
4-(isopropenyloxycarbonyl)-6-methoxy-3-methylthiomethyl-3,4-dihydro-1,4,5-triazanaphthalene-2(1H)-thione
6-chloro-4-(isopropyloxycarbonyl)-3-methylthiomethyl-3,4-dihydro-1,4,5-triazanaphthalen-2(1H)-one
6-chloro-4-(isopropyloxycarbonyl)-3-methylthiomethyl-3,4-dihydro-1,4,5-triazanaphthalene-2(1H)-thione
4-(isopropyloxycarbonyl)-6-methoxy-3-methylthiomethyl-3,4-dihydro-1,4,5-triazanaphthalen-2(1H)-one
4-(isopropyloxycarbonyl)-6-methoxy-3-methylthiomethyl-3,4-dihydro-1,4,5-triazanaphthalene-2(1H)-thione
4-acetyl-3-phenyl-3,4-dihydro-1,4,5-triazanaphthalen-2(1H)-one
4-(isopropenyloxycarbonyl)-3-phenyl-3,4-dihydro-1,4,5-triazanaphthalen-2(1H)-one
4-(isopropenyloxycarbonyl)-3-phenyl-3,4-dihydro-1,4,5-triazanaphthalene-2(1H)-thione
4-(isopropenyloxycarbonyl)-3-(2,6-dichlorophenyl)-3,4-dihydro-1,4,5-triazanaphthalen-2(1H)-one
4-(isopropenyloxycarbonyl)-3-(2,6-dichlorophenyl)-3,4-dihydro-1,4,5-triazanaphthalene-2(1H)-thione
4-(isopropyloxycarbonyl)-3-(2,6-dichlorophenyl)-3,4-dihydro-1,4,5-triazanaphthalen-2(1H)-one
4-(isopropyloxycarbonyl)-3-(2,6-dichlorophenyl)-3,4-dihydro-1,4,5-triazanaphthalene-2(1H)-thione
1-(isopropenyloxycarbonyl)-2-methylthiomethyl-1,2-dihydro-1,4,6-triazanaphthalen-3(4H)-one
1-(isopropenyloxycarbonyl)-2-methylthiomethyl-1,2-dihydro-1,4,6-triazanaphthalene-3(4H)-thione
1-(isopropyloxycarbonyl)-2-methylthiomethyl-1,2-dihydro-1,4,6-triazanaphthalen-3(4H)-one
1-(isopropyloxycarbonyl)-2-methylthiomethyl-1,2-dihydro-1,4,6-triazanaphthalene-3(4H)-thione
2-(ethoxycarbonylmethyl)-1-(isopropyloxycarbonyl)-1,2-dihydro-1,4,6-triazanaphthalen-3(4H)-one
3-(ethoxycarbonylmethyl)-4-(isopropyloxycarbonyl)-3,4-dihydro-1,4,5-triazanaphthalen-2(1H)-one
6-chloro-3-(ethoxycarbonylmethyl)-4-(isopropyloxycarbonyl)-3,4-dihydro-1,4,5-triazanaphthalen-2(1H)-one
3-(ethoxycarbonylmethyl)-4-(isopropyloxycarbonyl)-6-methoxy-3,4-dihydro-1,4,5-triazanaphthalen-2(1H)-one
6-dimethylamino-3-(ethoxycarbonylmethyl)-3,4-dihydro-1,4,5-triazanaphthalen-2(1H)-one
6-dimethylamino-3-(ethoxycarbonylmethyl)-4-(isopropyloxycarbonyl)-3,4-dihydro-1,4,5-triazanaphthalen-2(1H)-one
5,8-di(trifluoromethyl)-4-(isopropenyloxycarbonyl)-3,4-dihydro-1,4,6,7-tetraazanaphthalen-2(1H)-one
5,8-dichloro-4-(isopropenyloxycarbonyl)-3-methyl-3,4-dihydro-1,4,6,7-tetraazanaphthalen-2(1H)-one
5-chloro-4-(isopropyloxycarbonyl)-3-methylthiomethyl-3,4-dihydro-1,4,6,7-tetraazanaphthalen-2(1H)-one
5-chloro-4-(isopropyloxycarbonyl)-3-methylthiomethyl-3,4-dihydro-1,4,6,7-tetraazanaphthalene-2(1H)-thione
8-chloro-4-(isopropyloxycarbonyl)-3-methylthiomethyl-3,4-dihydro-1,4,6,7-tetraazanaphthalen-2(1H)-one
8-chloro-4-(isopropyloxycarbonyl)-3-methylthiomethyl-3,4-dihydro-1,4,6,7-tetraazanaphthalene-2(1H)-thione
4-(isopropyloxycarbonyl)-5-methoxy-3-methylthiomethyl-3,4-dihydro-1,4,6,7-tetraazanaphthalen-2(1H)-one
4-(isopropyloxycarbonyl)-5-methoxy-3-methylthiomethyl-3,4-dihydro-1,4,6,7-tetraazanaphthalene-2(1H)-thione
4-(isopropyloxycarbonyl)-8-methoxy-3-methylthiomethyl-3,4-dihydro-1,4,6,7-tetraazanaphthalen-2(1H)-one
4-(isopropyloxycarbonyl)-8-methoxy-3-methylthiomethyl-3,4-dihydro-1,4,6,7-tetraazanaphthalene-2(1H)-thione
5-chloro-4-(isopropyloxycarbonyl)-3-methylthiomethyl-3,4-dihydro-1,4,6,7-tetraazanaphthalen-2(1H)-one
5-chloro-4-(isopropyloxycarbonyl)-3-methylthiomethyl-3,4-dihydro-1,4,6,7-tetraazanaphthalene-2(1H)-thione
8-chloro-4-(isopropyloxycarbonyl)-3-methylthiomethyl-3,4-dihydro-1,4,6,7-tetraazanaphthalen-2(1H)-one
8-chloro-4-(isopropyloxycarbonyl)-3-methylthiomethyl-3,4-dihydro-1,4,6,7-tetraazanaphthalene-2(1H)-thione
4-(isopropyloxycarbonyl)-5-methoxy-3-methylthiomethyl-3,4-dihydro-1,4,6,7-tetraazanaphthalen-2(1H)-one
4-(isopropyloxycarbonyl)-5-methoxy-3-methylthiomethyl-3,4-dihydro-1,4,6,7-tetraazanaphthalene-2(1H)-thione
4-(isopropyloxycarbonyl)-8-methoxy-3-methylthiomethyl-3,4-dihydro-1,4,6,7-tetraazanaphthalen-2(1H)-one
4-(isopropyloxycarbonyl)-8-methoxy-3-methylthiomethyl-3,4-dihydro-1,4,6,7-tetraazanaphthalene-2(1H)-thione
4-(isopropenyloxycarbonyl)-3-methyl-3,4-dihydro-1,4,5,7-tetraazanaphthalen-2(1H)-one
4-(isopropenyloxycarbonyl)-3-methyl-3,4-dihydro-1,4,5,7-tetraazanaphthalene-2(1H)-thione 4-(isopropenyloxycarbonyl)-3,3-dimethyl-3,4-dihydro-1,4,5,7-tetraazanaphthalen-2(1H)-one
4-(isopropenyloxycarbonyl)-3,3-dimethyl-3,4-dihydro-1,4,5,7-tetraazanaphthalene-2(1H)-thione
4-(isopropyloxycarbonyl)-3-methylthiomethyl-3,4-dihydro-1,4,5,7-tetraazanaphthalen-2(1H)-one
4-(isopropyloxycarbonyl)-3-methylthiomethyl-3,4-dihydro-1,4,5,7-tetraazanaphthalene-2(1H)-thione
6-chloro-4-(isopropenyloxycarbonyl)-3-methyl-3,4-dihydro-1,4,5,7-tetraazanaphthalen-2(1H)-one
6-chloro-4-(isopropenyloxycarbonyl)-3-methyl-3,4-dihydro-1,4,5,7-tetraazanaphthalene-2(1H)-thione
6-chloro-4-(isopropenyloxycarbonyl)-3,3-dimethyl-3,4-dihydro-1,4,5,7-tetraazanaphthalen-2(1H)-one
6-chloro-4-(isopropenyloxycarbonyl)-3,3-dimethyl-3,4-dihydro-1,4,5,7-tetraazanaphthalene-2(1H)-thione
6-chloro-4-(isopropyloxycarbonyl)-3-methylthiomethyl-3,4-dihydro-1,4,5,7-tetraazanaphthalen-2(1H)-one
6-chloro-4-(isopropyloxycarbonyl)-3-methylthiomethyl-3,4-dihydro-1,4,5,7-tetraazanaphthalene-2(1H)-thione
6-amino-4-(isopropenyloxycarbonyl)-3-methyl-3,4-dihydro-1,4,5,7-tetraazanaphthalen-2(1H)-one
6-amino-4-(isopropenyloxycarbonyl)-3-methyl-3,4-dihydro-1,4,5,7-tetraazanaphthalene-2(1H)-thione
6-amino-4-(isopropenyloxycarbonyl)-3,3-dimethyl-3,4-dihydro-1,4,5,7-tetraazanaphthalen-2(1H)-one
6-amino-4-(isopropenyloxycarbonyl)-3,3-dimethyl-3,4-dihydro-1,4,5,7-tetraazanaphthalene-2(1H)-thione
6-amino-4-(isopropyloxycarbonyl)-3-methylthiomethyl-3,4-dihydro-1,4,5,7-tetraazanaphthalen-2(1H)-one
6-amino-4-(isopropyloxycarbonyl)-3-methylthiomethyl-3,4-dihydro-1,4,5,7-tetraazanaphthalene-2(1H)-thione
4-(isopropenyloxycarbonyl)-6-methoxy-3-methyl-3,4-dihydro-1,4,5,7-tetraazanaphthalen-2(1H)-one
4-(isopropenyloxycarbonyl)-6-methoxy-3-methyl-3,4-dihydro-1,4,5,7-tetraazanaphthalene-2(1H)-thione
4-(isopropenyloxycarbonyl)-3,3-dimethyl-6-methoxy-3,4-dihydro-1,4,5,7-tetraazanaphthalen-2(1H)-one
4-(isopropenyloxycarbonyl)-3,3-dimethyl-6-methoxy-3,4-dihydro-1,4,5,7-tetraazanaphthalene-2(1H)-thione
4-(isopropyloxycarbonyl)-6-methoxy-3-methylthiomethyl-3,4-dihydro-1,4,5,7-tetraazanaphthalen-2(1H)-one
4-(isopropyloxycarbonyl)-6-methoxy-3-methylthiomethyl-3,4-dihydro-1,4,5,7-tetraazanaphthalene-2(1H)-thione
1-(isopropenyloxycarbonyl)-2-methyl-1,2-dihydro-1,4,5,7-tetraazanaphthalen-3(4H)-one
1-(isopropenyloxycarbonyl)-2-methyl-1,2-dihydro-1,4,5,7-tetraazanaphthalene-3(4H)-thione
1-(isopropenyloxycarbonyl)-2,2-dimethyl-1,2-dihydro-1,4,5,7-tetraazanaphthalen-3(4H)-one
1-(isopropenyloxycarbonyl)-2,2-dimethyl-1,2-dihydro-1,4,5,7-tetraazanaphthalene-3(4H)-thione
1-(isopropyloxycarbonyl)-2-methylthiomethyl-1,2-dihydro-1,4,5,7-tetraazanaphthalen-3(4H)-one
1-(isopropyloxycarbonyl)-2-methylthiomethyl-1,2-dihydro-1,4,5,7-tetraazanaphthalene-3(4H)-thione
4-(isopropyloxycarbonyl)-3-methyl-3,4-dihydro-1,4,5,7-tetraazanaphthalene-2(1H)-thione
4-(isopropenyloxycarbonyl)-6-[1-(methoxycarbonyl)ethylamino]-3-methyl-3,4-dihydro-1,4,5-triazanaphthalen-2(1H)-one

We claim:

1. A compound of the formula I

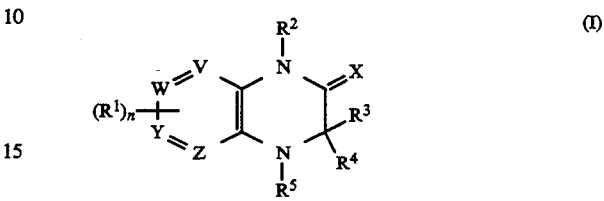

and its tautomeric form of the formula Ia

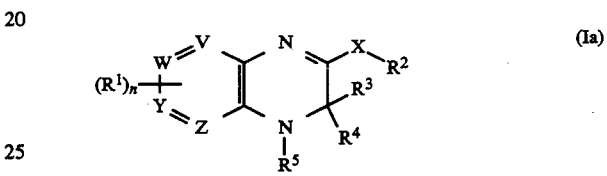

in which:
n is zero or one,
the individual $R^1$ substituents are, independently of one another, fluorine, chlorine, trifluoromethyl, hydroxyl, mercapto, $C_1$–$C_3$-alkyl, $C_1$–$C_3$-alkoxy, $C_1$–$C_3$-alkylthio, amino, $C_1$–$C_3$-alkylamino, di($C_1$–$C_3$-alkyl)amino, ($C_1$–$C_2$-alkyl)oxycarbonyl($C_1$–$C_4$-alkyl)amino, $C_1$–$C_3$-acylamino,
V, W, Y and Z are CH, $CR^1$ or N, where the ring contains one nitrogen atom,
X is oxygen or sulfur,
$R^2$ and $R^5$ can be identical or different and be independently of one another, hydrogen, hydroxyl, $C_1$–$C_3$-alkyl, $C_2$–$C_6$-alkenyl, $C_1$–$C_4$-alkyloxycarbonyl, $C_2$–$C_4$-alkenyloxycarbonyl,
or a 2-, 3- or 4-picolyl radical,
$R^3$ and $R^4$ can be identical or different and be independently of one another, hydrogen, $C_1$–$C_4$-alkyl optionally substituted by $C_1$–$C_2$-alkylthio, $C_1$–$C_2$-alkylsulfonyl or $C_1$–$C_2$-alkylsulfinyl;
with the exception of the compounds in which $R^2$ and $R^5$ or $R^3$ and $R^4$ are simultaneously hydrogen.

2. A pharmaceutical composition containing an effective amount of at least one compound of the formula I or Ia as claimed in claim 1, together with a pharmaceutically acceptable carrier.

3. A method for the treatment of viral diseases which comprises administering to a host in need of said treatment a pharmaceutical composition as claimed in claim 2.

4. A method for the treatment of viral diseases which comprises administering to a host in need of said treatment an effective amount of a compound of the formula I or Ia as claimed in claim 1.

* * * * *